United States Patent [19]
Shturman et al.

[11] Patent Number: 6,132,444
[45] Date of Patent: *Oct. 17, 2000

[54] ECCENTRIC DRIVE SHAFT FOR ATHERECTOMY DEVICE AND METHOD FOR MANUFACTURE

[75] Inventors: Leonid Shturman, Minneapolis, Minn.; Andrei Nevzorov; Mikhail Spassky, both of Moscow, Russian Federation

[73] Assignee: Shturman Cardiology Systems, Inc., Minneapolis, Minn.

[ * ] Notice: This patent is subject to a terminal disclaimer.

[21] Appl. No.: 09/044,550

[22] Filed: Mar. 19, 1998

Related U.S. Application Data

[63] Continuation-in-part of application No. 08/911,586, Aug. 14, 1997.
[51] Int. Cl.⁷ .................................................. A61B 17/00
[52] U.S. Cl. ........................................... 606/159; 128/858
[58] Field of Search ............................... 606/1, 159, 170, 606/171, 180; 604/22; 128/898

[56] References Cited

U.S. PATENT DOCUMENTS

| | | |
|---|---|---|
| 4,030,503 | 6/1977 | Clark, III . |
| 4,883,460 | 11/1989 | Zanetti . |
| 4,990,134 | 2/1991 | Auth . |
| 5,158,564 | 10/1992 | Schnepp-Pesch et al. . |
| 5,192,291 | 3/1993 | Pennek, Jr. . |
| 5,217,474 | 6/1993 | Zacca et al. . |
| 5,308,354 | 5/1994 | Zacca et al. . |
| 5,312,427 | 5/1994 | Shturman . |
| 5,314,438 | 5/1994 | Shturman ................................. 606/159 |
| 5,356,418 | 10/1994 | Shturman . |
| 5,358,485 | 10/1994 | Vance et al. . |
| 5,360,432 | 11/1994 | Shturman . |
| 5,395,311 | 3/1995 | Andrews . |
| 5,490,859 | 2/1996 | Mische et al. . |
| 5,501,694 | 3/1996 | Ressemann et al. . |
| 5,554,163 | 9/1996 | Shturman . |
| 5,681,336 | 10/1997 | Clement et al. ........................ 606/159 |
| 5,843,103 | 12/1998 | Wulfman . |
| 5,897,566 | 4/1999 | Shturman . |

FOREIGN PATENT DOCUMENTS

| | | |
|---|---|---|
| 0 421 457 B1 | 4/1991 | European Pat. Off. . |
| 91 06 690 | 8/1991 | Germany . |
| 2055991 C1 | 10/1996 | Russian Federation . |
| 2069540 | 11/1996 | Russian Federation . |
| 2080454 | 5/1997 | Russian Federation . |
| WO 94/08519 | 4/1994 | WIPO . |
| WO 94/09709 | 5/1994 | WIPO . |
| WO 98/02101 | 1/1998 | WIPO . |

*Primary Examiner*—Michael Buiz
*Assistant Examiner*—William W. Lewis
*Attorney, Agent, or Firm*—Fredrikson & Byron, PA

[57] ABSTRACT

A method of manufacturing a rotational atherectomy drive shaft having an asymmetrical tissue removal section. One or more strands of wire are helically wound about an elongated mandrel having an enlarged diameter section with a predetermined shape, thereby forming an elongated, flexible drive shaft which has an enlarged diameter tissue removal section. A portion of the drive shaft, including the enlarged diameter tissue removal section, is placed into a first clamp and given a first heat treatment to give the wire turns of the enlarged diameter tissue removal section an initial set, thereby preserving the initial shape of the enlarged diameter tissue removal section of the drive shaft. The drive shaft is then removed from the first clamp and the mandrel is dissolved. The enlarged diameter section of the drive shaft is then deformed to an asymmetrical shape by placing a portion of the drive shaft, including the enlarged diameter tissue removal section, into a second clamp. The clamped portion of the drive shaft is then heat treated for a second time to give wire turns of the enlarged diameter tissue removal section a new set, thereby preserving the asymmetrical shape of the enlarged diameter section. In its asymmetrical shape the enlarged diameter tissue removal section has a longitudinally flat "side"—i.e., all wire turns of the tissue removal section may be connected by an imaginary straight line which throughout its length is parallel to the rotational axis of the drive shaft.

81 Claims, 36 Drawing Sheets

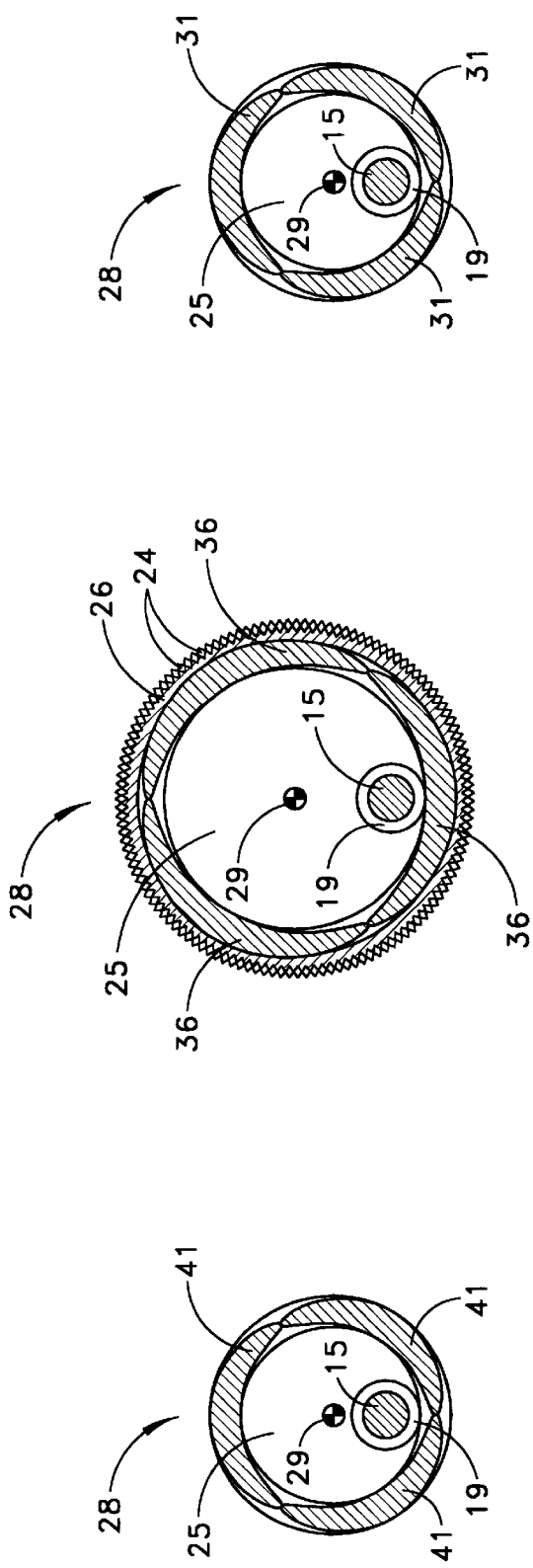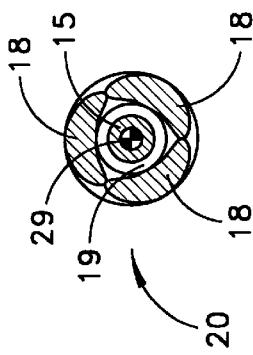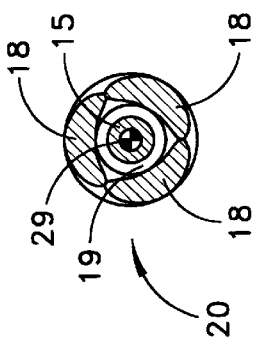
FIG. 4A  FIG. 4B  FIG. 4C  FIG. 4D  FIG. 4E

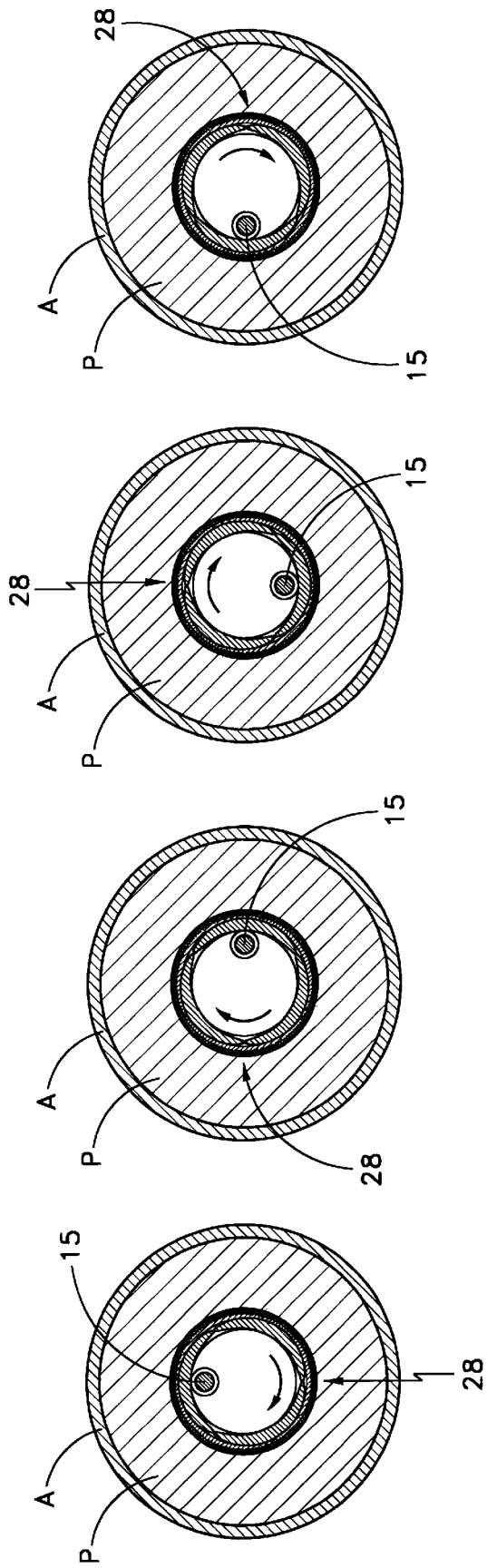

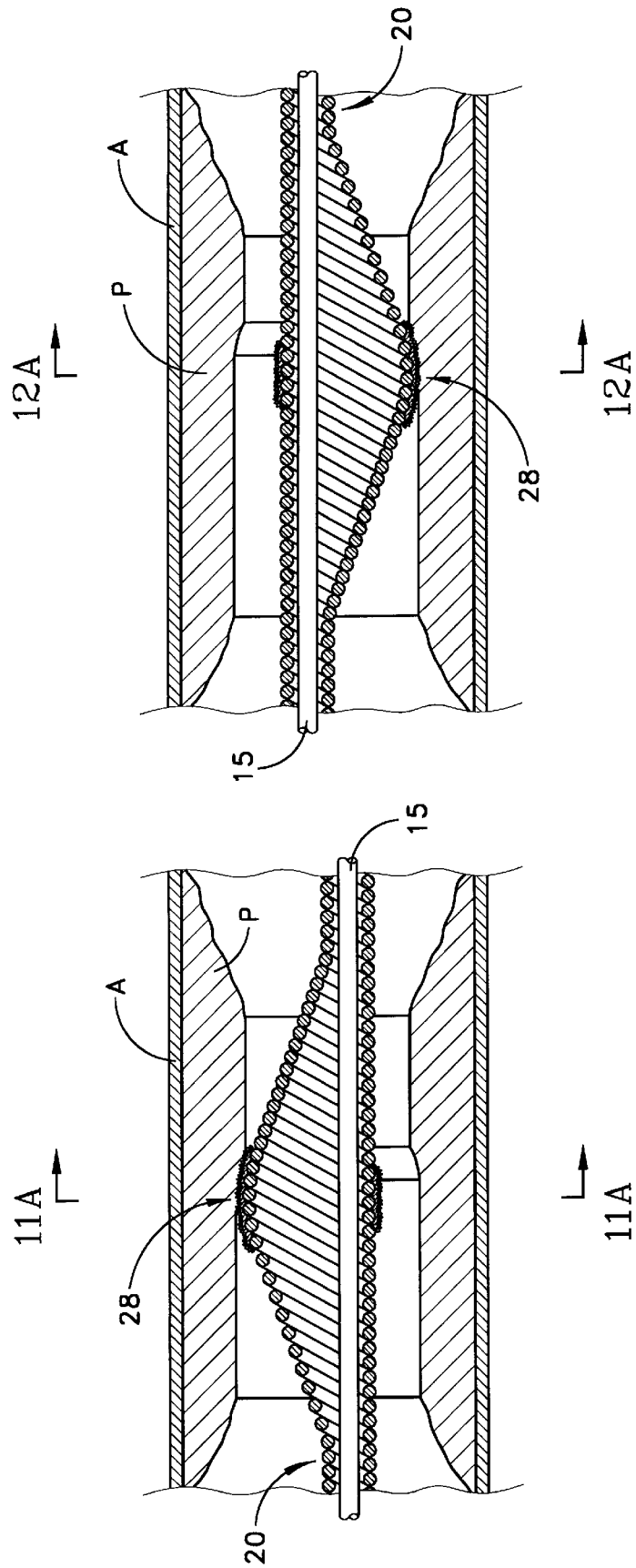

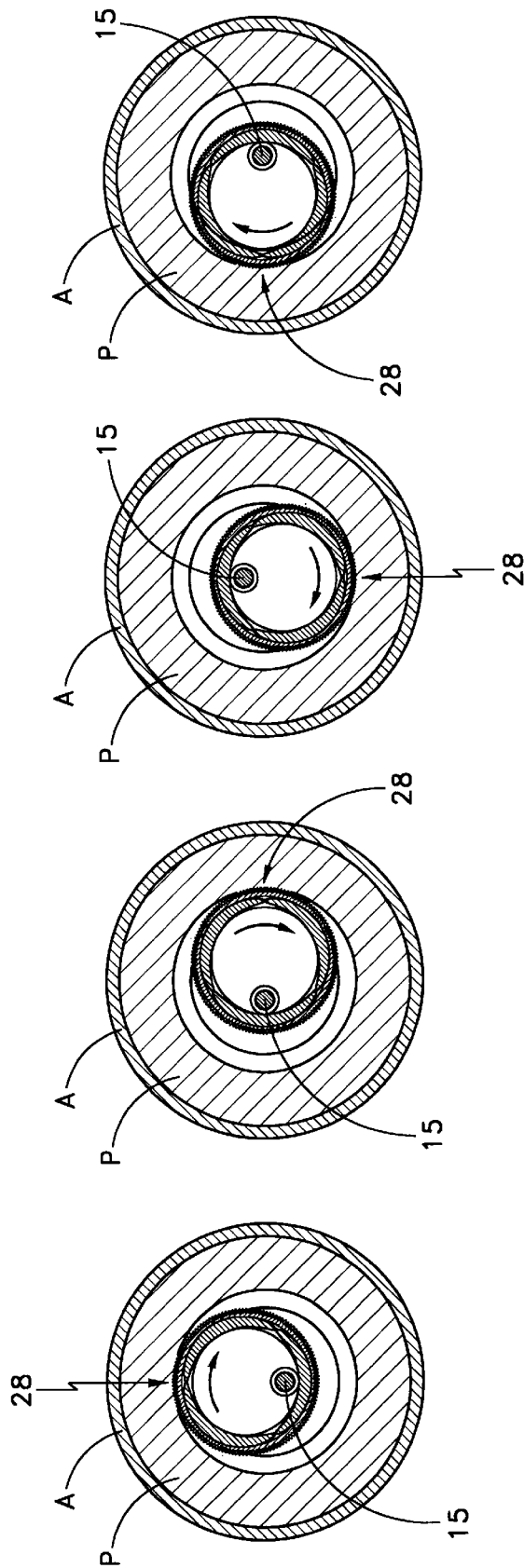

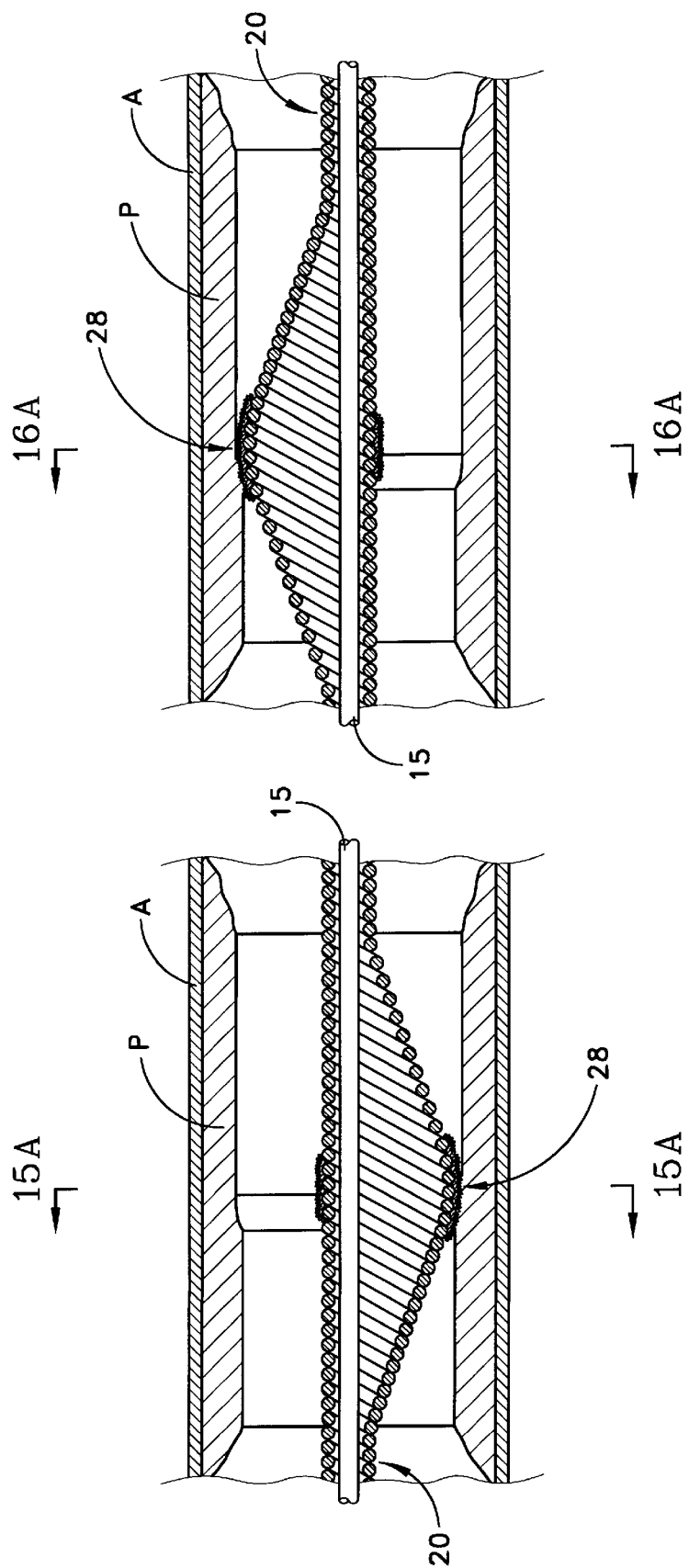

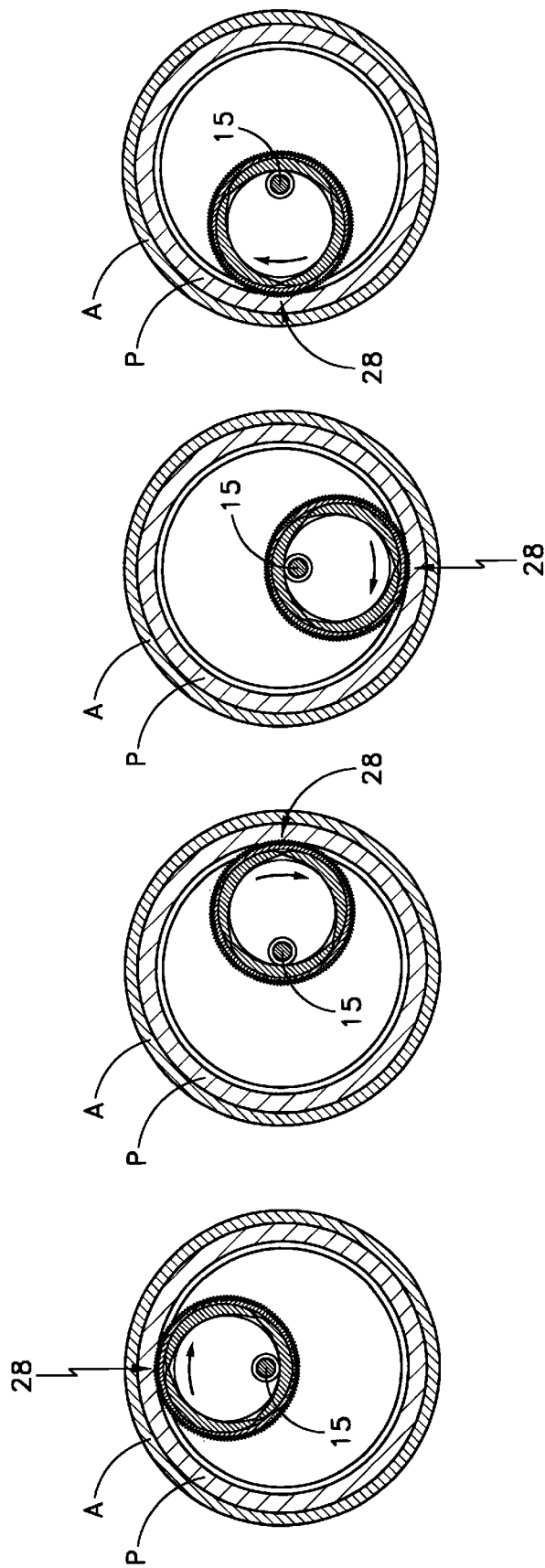

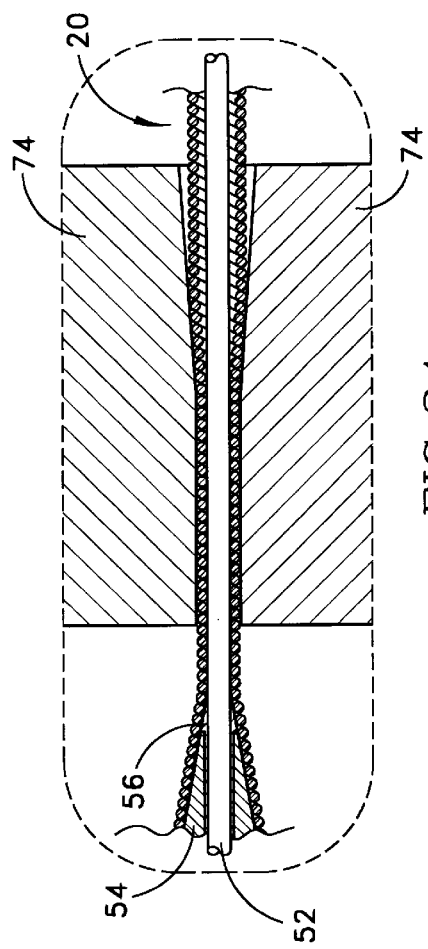
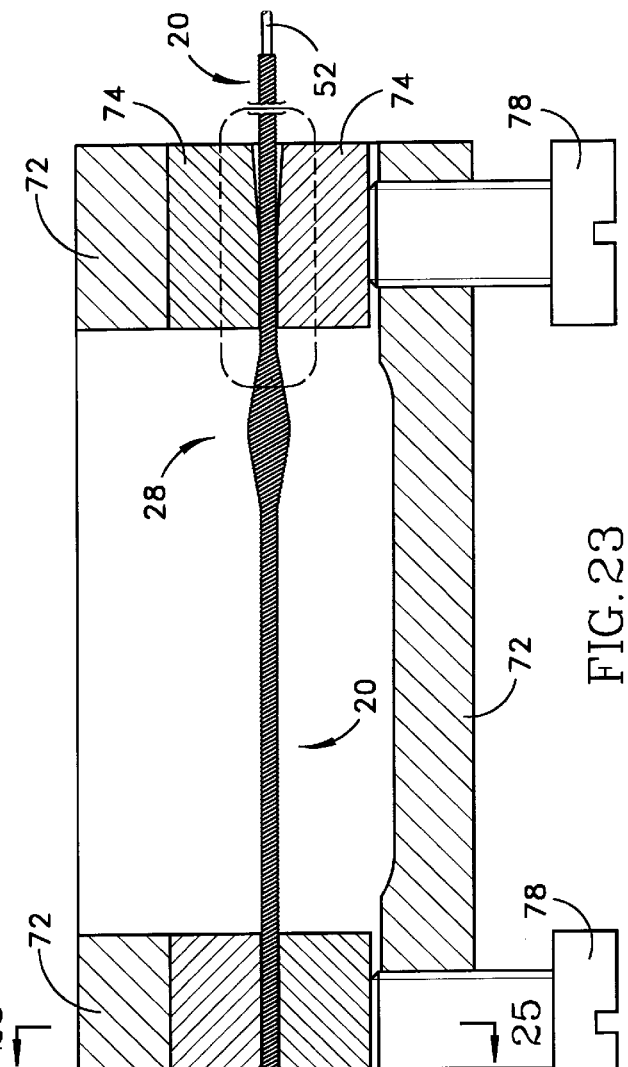
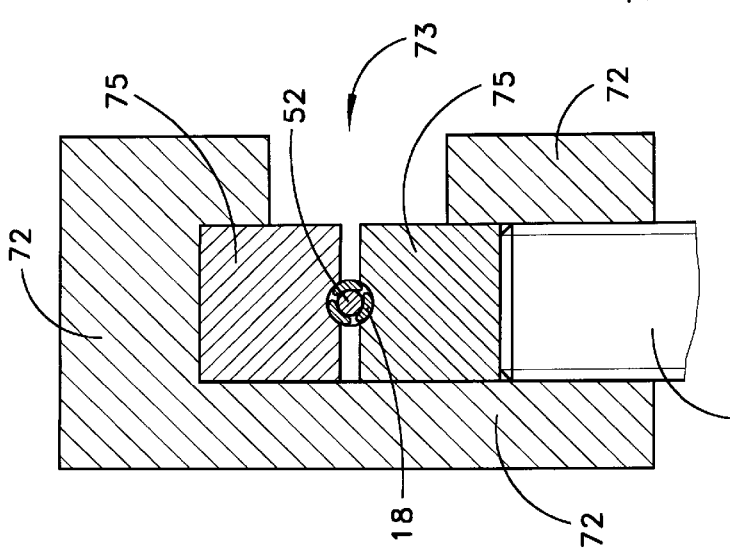
FIG. 24
FIG. 23
FIG. 25

ECCENTRIC DRIVE SHAFT FOR ATHERECTOMY DEVICE AND METHOD FOR MANUFACTURE

CROSS REFERENCE TO RELATED APPLICATION

This application is a continuation in part of copending U.S. patent application Ser. No. 08/911,586, filed Aug. 14, 1997, the contents of which are hereby incorporated by reference.

TECHNICAL FIELD

The invention relates to devices and methods for removing tissue from body passageways, such as removal of atherosclerotic plaque from arteries, utilizing a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience in-stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive cutting material such as diamond particles is carried at the distal end of a flexible drive shaft. The burr is rotated at high speeds (typically, e.g., in the range of about 140,000–180,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) shows another atherectomy device having a drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged diameter section of the drive shaft.

Co-pending U.S. patent application Ser. No. 08/911,586, filed Aug. 14, 1997, describes a rotational atherectomy device having a flexible, elongated, rotatable drive shaft with an eccentric enlarged diameter section. At least part of the eccentric enlarged diameter section has a tissue removing surface—typically an abrasive surface—to define a tissue removing segment of the drive shaft. When placed within an artery against stenotic tissue and rotated at sufficiently high speeds (e.g., in the range of about 20,000 rpm to about 200,000 rpm) the eccentric nature of the enlarged diameter section of the drive shaft causes such section to rotate in such a fashion as to open the stenotic lesion to a diameter substantially larger than the outer diameter of the enlarged diameter section. Preferably the eccentric enlarged diameter section of the drive shaft has a center of mass spaced radially from the rotational axis of the drive shaft, facilitating the ability of the device to open the stenotic lesion to a diameter substantially larger than the outer diameter of the enlarged diameter section. Typically this is achieved by constructing the enlarged diameter section of the drive shaft asymmetrically—i.e., spacing the geometric center of the eccentric enlarged diameter section of the drive shaft away from the rotational axis of the drive shaft. A drive shaft having an eccentric enlarged diameter tissue removal section with a diameter of not more than 2 mm is capable of opening stenotic lesions to a diameter equal to the original diameter of the main coronary arteries (i.e., to a diameter of more than 3 mm) so that in a significant percentage of cases balloon angioplasty may not be needed to complete the procedure. The device is particularly useful for cleaning out partially blocked stents.

SUMMARY OF THE INVENTION

The invention provides an improved method of manufacturing a drive shaft having an asymmetrical tissue removal section. One or more strands of wire are helically wound about an elongated mandrel having an enlarged diameter section with a predetermined shape, thereby forming an elongated, flexible drive shaft which has an enlarged diameter tissue removal section defined by wire turns of the drive shaft and having an initial shape which corresponds to the shape of the enlarged diameter section of the mandrel. A portion of the drive shaft, including the enlarged diameter tissue removal section, is placed into a first clamp and heat treated (the "first heat treatment") to give the wire turns of the enlarged diameter tissue removal section an initial set, thereby preserving the initial shape of the enlarged diameter tissue removal section of the drive shaft.

The drive shaft is then removed from the first clamp and at least the enlarged diameter tissue removal section of the drive shaft is immersed into a solution of nitric acid to dissolve at least the enlarged diameter section of the mandrel from within the drive shaft (preferably the entire drive shaft is so immersed, thereby dissolving the entire mandrel).

The enlarged diameter section of the drive shaft is then deformed to an asymmetrical shape by placing a portion of the drive shaft, including the enlarged diameter tissue removal section, into a second clamp. The clamped portion of the drive shaft is then heat treated for a second time (the "second heat treatment") to give wire turns of the enlarged diameter tissue removal section a new set, thereby preserving the asymmetrical shape of the enlarged diameter section.

Preferably the deformation of the enlarged diameter tissue removal section to its asymmetrical shape is such that in its desired shape the enlarged diameter tissue removal section has a longitudinally flat "side"—i.e., all wire turns of the tissue removal section may be connected by an imaginary straight line which throughout its length is parallel to the rotational axis of the drive shaft. This shape of the tissue removal section of the drive shaft is even more asymmetrical than the tissue removal section of the device described in application Ser. No. 08/911,586 referred to above, thereby facilitating faster opening of stenotic lesions to an even larger diameter.

BRIEF DESCRIPTION OF THE DRAWINGS

FIGS. 4A–4E are transverse cross-sectional views of FIG. 4, taken along lines 4A—4A through 4E—4E thereof;

FIG. 7A is a transverse cross-sectional view of FIG. 5, taken along lines 7A—7A thereof;

FIG. 7B is a transverse cross-sectional view similar to FIG. 7A, showing the rotating enlarged diameter section of the drive shaft in a moved position;

FIG. 8A is a transverse cross-sectional view of FIG. 6, taken along lines 8A—8A thereof;

FIG. 8B is a transverse cross-sectional view similar to FIG. 8A, showing the rotating enlarged diameter section of the drive shaft in a moved position;

FIGS. 9–10 are longitudinal cross-sectional views similar to FIGS. 5–6 showing the rotating enlarged diameter section of the drive shaft being moved proximally across the stenotic lesion, which has now been partially opened;

FIG. 11A is a transverse cross-sectional view of FIG. 9, taken along lines 11A—11A thereof;

FIG. 11B is a transverse cross-sectional view similar to FIG. 11A, showing the rotating enlarged diameter section of the drive shaft in a moved position;

FIG. 12A is a transverse cross-sectional view of FIG. 10, taken along lines 12A—12A thereof;

FIG. 12B is a transverse cross-sectional view similar to FIG. 12A, showing the rotating enlarged diameter section of the drive shaft in a moved position;

FIGS. 13–14 are longitudinal cross-sectional views similar to FIGS. 5–6 showing the rotating enlarged diameter section of the drive shaft being moved distally across the stenotic lesion, which has now been opened further;

FIG. 19A is a transverse cross-sectional view of FIG. 17, taken along lines 19A—19A thereof;

FIG. 19B is a transverse cross-sectional view similar to FIG. 19A, showing the rotating enlarged diameter section of the drive shaft in a moved position;

FIG. 20A is a transverse cross-sectional view of FIG. 18, taken along lines 18A—18A thereof;

FIG. 20B is a transverse cross-sectional view similar to FIG. 20A, showing the rotating enlarged diameter section of the drive shaft in a moved position;

FIG. 23 is a longitudinal cross-sectional view of the clamp of FIG. 22;

FIG. 24 is an enlarged view showing in longitudinal cross-section details of a portion of FIG. 23;

FIG. 25 is an enlarged cross-sectional view, partially broken away, of FIG. 23, taken along lines 25—25 thereof;

DETAILED DESCRIPTION OF THE INVENTION

Figure 1:
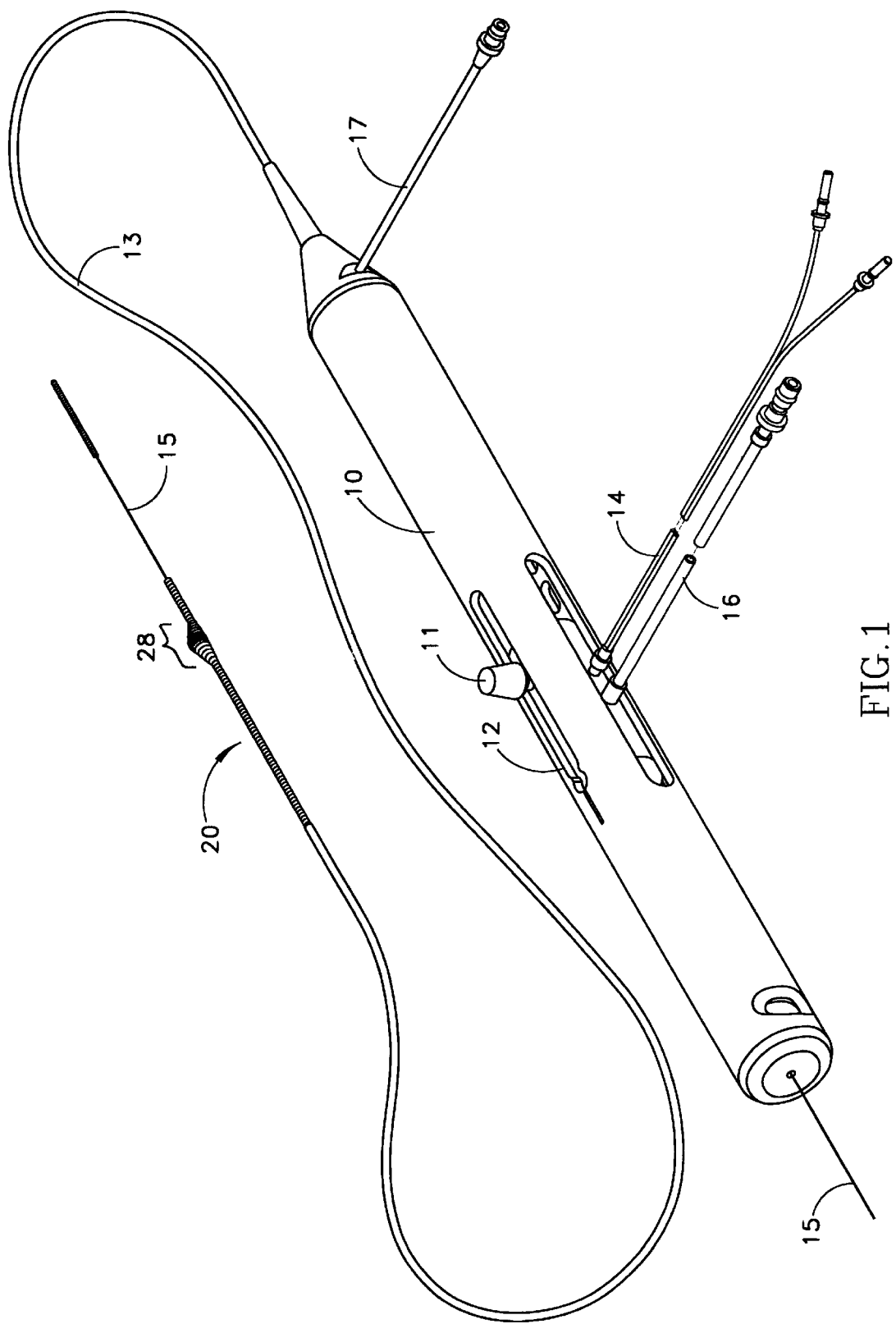
FIG. 1 is a perspective view of the rotational atherectomy device of the invention.
Figure 2:
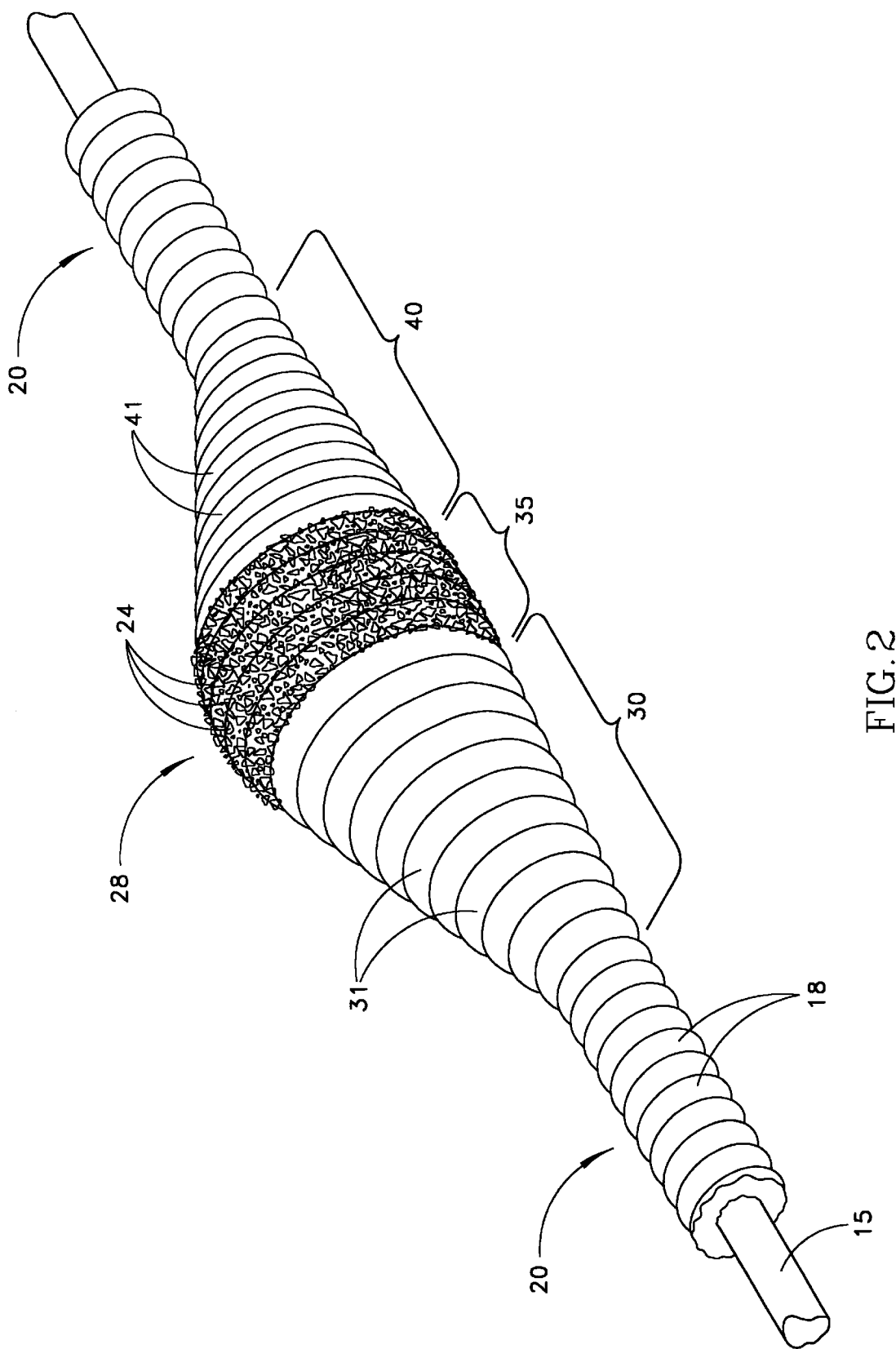
FIG. 2 is a perspective, broken-away view of an eccentric enlarged diameter section of the drive shaft of a rotational atherectomy device of the invention.
Figure 3:
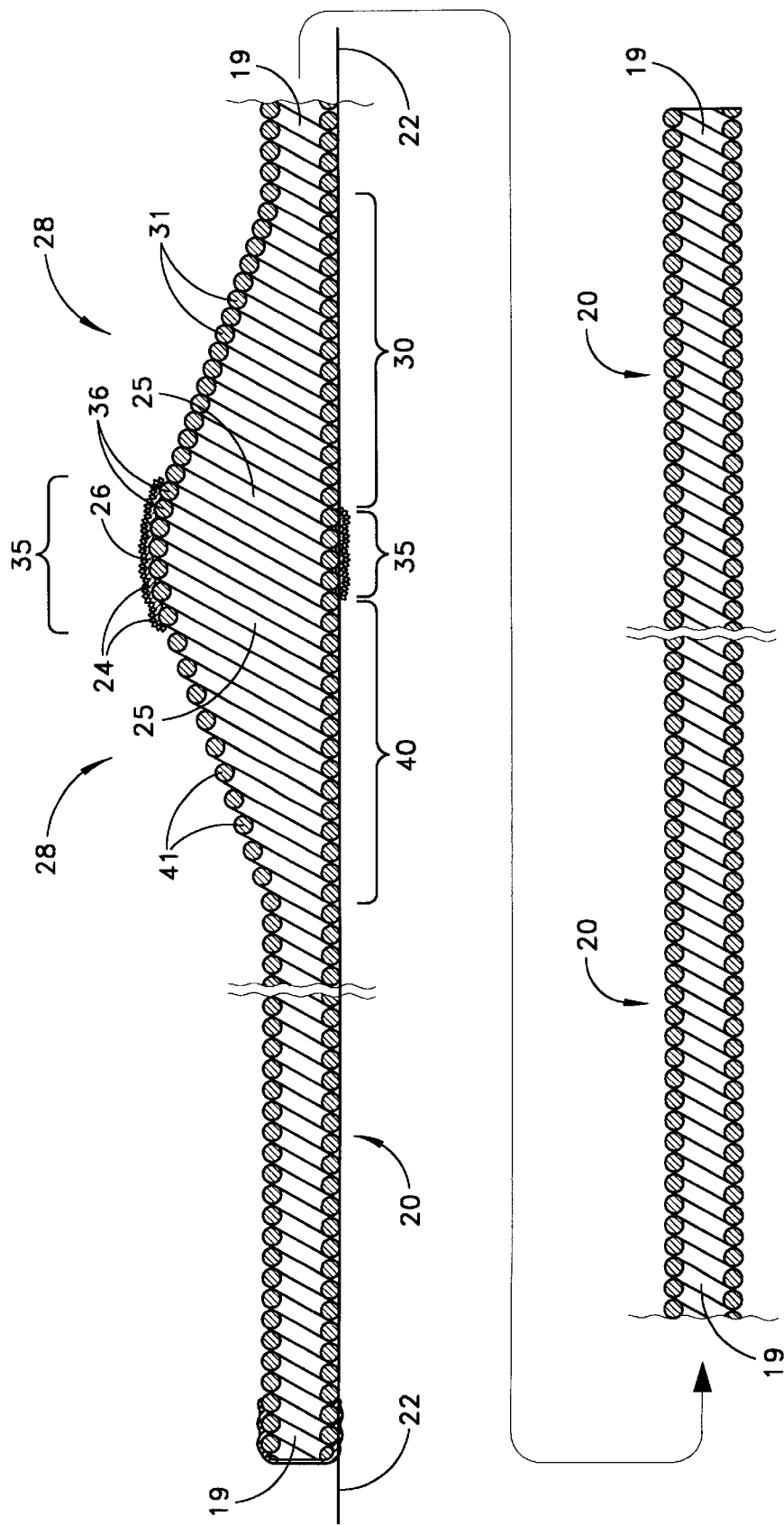
FIG. 3 is a broken-away, longitudinal cross-sectional view of the drive shaft of an atherectomy device of the invention.
Figure 4:
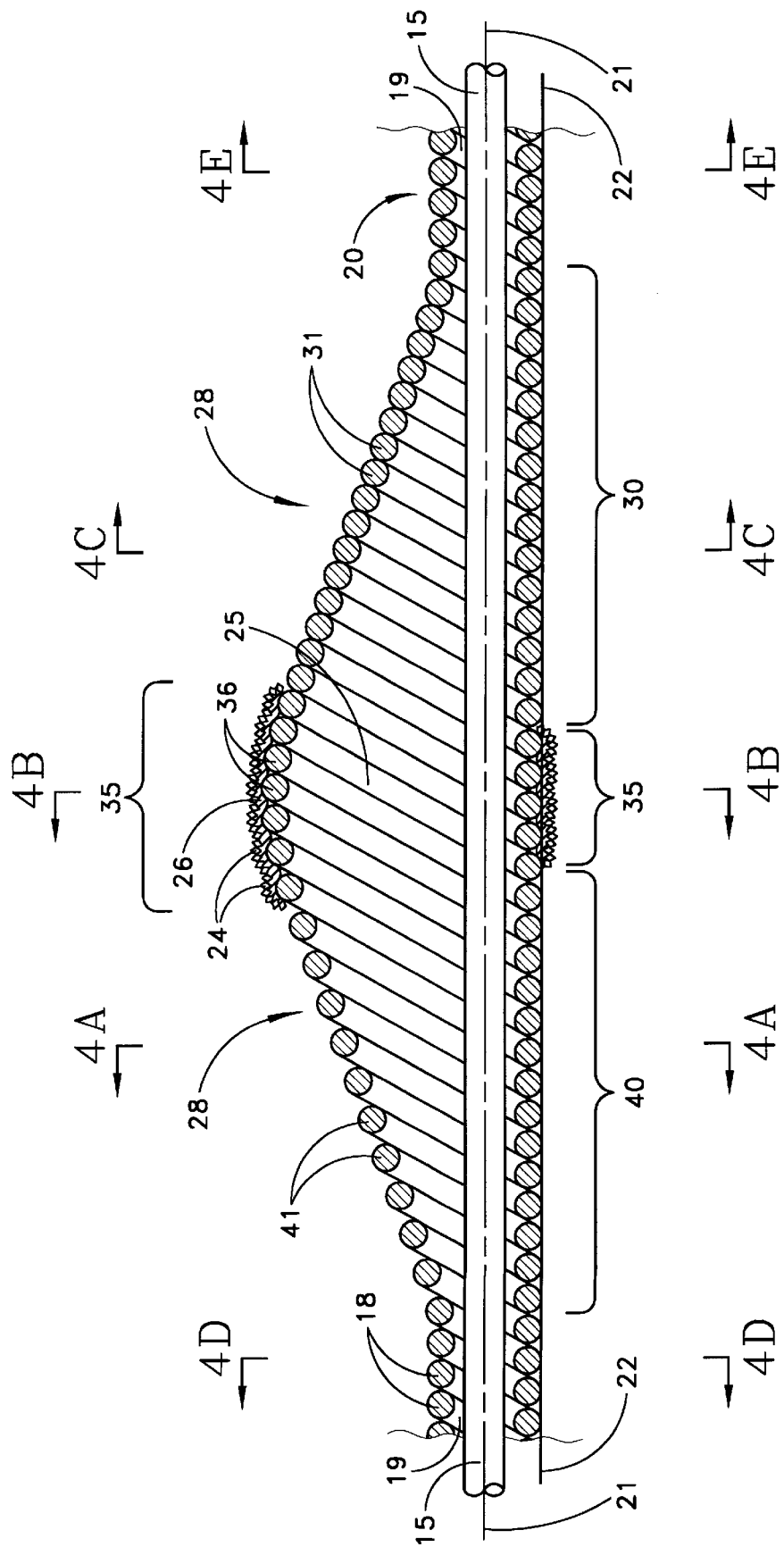
FIG. 4 is a broken-away, longitudinal cross-sectional view of the eccentric enlarged diameter section of the atherectomy device of the invention.

FIG. 1 illustrates a typical rotational atherectomy device of the invention. The device includes a handle portion 10, an elongated, flexible drive shaft 20 having an asymmetric enlarged diameter section 28, and an elongated catheter 13 extending distally from the handle portion 10. The drive shaft 20 and its asymmetric enlarged diameter section 28 are constructed from helically coiled wire. The catheter 13 has a lumen in which most of the length of the drive shaft 20 is disposed, except for its enlarged diameter section 28 and a short section distal to the enlarged diameter section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 14 may also be provided for monitoring the speed of rotation of the turbine and drive shaft 20 (details regarding such handles and associated instrumentation are well know in the industry, and are described, e.g., in U.S. Pat. No. 5,314,407, issued to Auth).

The handle 10 also desirably includes a control knob 11 for advancing and retracting the turbine and drive shaft 20 with respect to the catheter 13 and the body of the handle.

FIGS. 2–4 and 4A–4C illustrate details of the asymmetric enlarged diameter section 28 of one embodiment of the invention. For purposes of the present invention the terms "asymmetric" and "eccentric" are used interchangeably in reference to the enlarged diameter tissue removal section 28 of the drive shaft 20. The drive shaft 20 is comprised of one or more helically wound wires 18 which define a guide wire lumen 19 and a hollow cavity 25 within the enlarged diameter section 28. Except for the guide wire 15 traversing the hollow cavity 25, the hollow cavity 25 is substantially empty. The asymmetric enlarged diameter section 28 includes proximal 30, intermediate 35 and distal 40 portions. Wire turns 31 of the proximal portion 30 of the asymmetric enlarged diameter section 28 preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35 are provided with gradually changing diameters to provide one "side" of the asymmetric enlarged diameter section 28 with a generally convex outer surface which is shaped to provide a smooth transition between the proximal and distal conical portions of the enlarged diameter section 28 of the drive shaft 20.

At least part of the asymmetric enlarged diameter section 28 (preferably the intermediate portion 35) includes an external surface capable of removing tissue. Preferably the tissue removing surface comprises a coating of an abrasive material 24 to define a tissue removing segment of the drive shaft 20. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable bonding material 26—such attachment may be achieved using well known techniques, such as conventional electroplating technologies. The bonding material 26 may be a conventional bonding material such as nickel. Alternately, the bonding material may be gold, platinum, iridium, alloys of these metals, or other suitable radio-opaque materials (or at least a layer of one of these materials) to increase the radio-opacity of the enlarged diameter section 28 of the drive shaft. Alternately the external tissue removing surface may be simply a section of the wire turns which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface.

FIGS. 3, 4 and 4A–4C illustrate the particular geometry of one embodiment of an asymmetric enlarged diameter section 28 of the invention. The elongated drive shaft 20 has a rotational axis 21 (see FIG. 4) which is coaxial with the guide wire 15, the guide wire 15 being disposed within the lumen 19 of the drive shaft 20. The enlarged diameter tissue removal section has an asymmetrical (or eccentric) shape which has a longitudinally flat "side"—i.e., although in the circumferential direction the wire turns are curved, in the longitudinal direction the wire turns are aligned with respect to each other so that at one circumferential location all wire turns of the tissue removal section may be connected by an imaginary straight line 22. The imaginary line 22 throughout its length is parallel to the rotational axis 21 of the drive shaft 20. Another way of describing this configuration is to say that each wire turn of the enlarged diameter tissue removal section 28 includes a point on its outer surface that is collinear with a point on the outer surface of each other wire turn of the enlarged diameter tissue removal section 28, such points defining a straight line 22 that is parallel to the rotational axis 21 of the drive shaft 20. Yet another way of characterizing this configuration is that each wire turn of the enlarged diameter tissue removal section 28 includes a point on its outer surface that is spaced the same distance from the rotational axis 15 of the drive shaft 20 as a point on the outer surface of each other wire turn of the enlarged diameter tissue removal section 28.

FIGS. 4A–4C depict the positions of the centers of mass 29 of three cross-sectional slices (shown as faces of transverse cross-sections) of the eccentric enlarged diameter section 28. The entire eccentric enlarged diameter section 28 may be divided into many such thin slices, each slice having its own center of mass. FIG. 4B is taken at a position where the eccentric enlarged diameter section 28 has its maximum cross-sectional diameter (which, in this case, is the maximum diameter of the intermediate portion 35 of the eccentric enlarged diameter section 28), and FIGS. 4A and 4C are taken, respectively in the distal 40 and proximal 30 portions of the eccentric enlarged diameter section 28. In each of these cross-sectional slices the center of mass 29 is spaced away from the rotational axis of the drive shaft, the rotational axis of the drive shaft 20 coinciding with the center of the guide wire 15. The center of mass 29 of each cross-sectional slice also generally coincides with the geometric center of such cross-sectional slice. FIG. 4B shows the slice having the greatest cross-sectional diameter. In this slice both the center of mass 29 and the geometric center are located the farthest (i.e., maximally spaced away) from the rotational axis of the drive shaft. Of course, the center of mass of the entire enlarged diameter section is a composite of the individual centers of mass of multiple slices of the enlarged diameter section, and the overall center of mass will, therefore, be closer to the axis of rotation of the drive shaft than the center of mass of the slice depicted in FIG. 4B. FIGS. 4D–4E illustrate the fact that both the centers of mass 29 and the geometric centers of those slices of the drive shaft 20 which are taken both proximally and distally of the eccentric enlarged diameter section 28 coincide with the center of the guide wire 15 and, thus, the rotational axis 21 of the drive shaft 20. Therefore, such portions of the drive shaft located proximally and distally of the enlarged diameter section 28 are not eccentric (i.e., they are symmetrical and balanced) with respect to the rotational axis 21 of the drive shaft 20.

FIGS. 5–20B illustrate a series of steps in which the eccentric rotational atherectomy device of the invention is used to open a stenotic lesion to a diameter substantially larger than the nominal diameter of the eccentric enlarged diameter section 28 of the drive shaft 20.

Figures 5, 6:
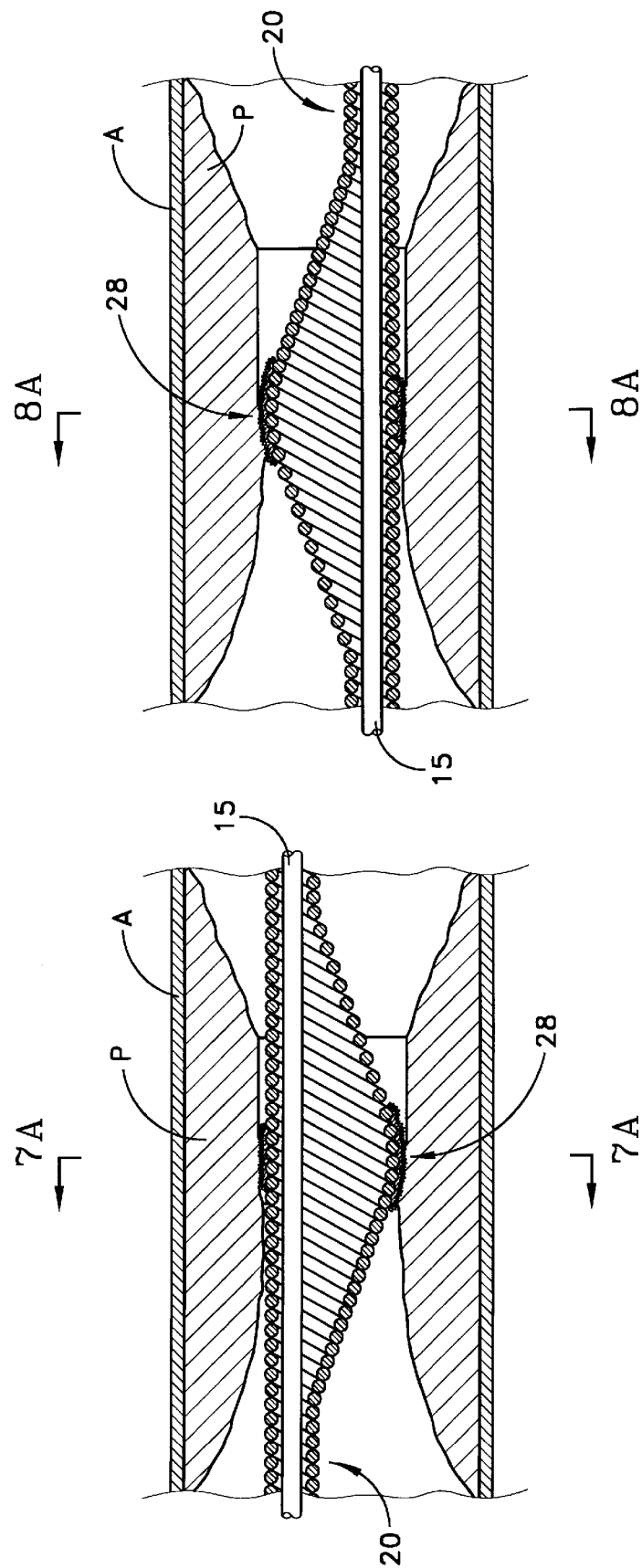
FIGS. 5–6 are longitudinal cross-sectional views showing the rotating enlarged diameter section of the drive shaft being moved distally across a stenotic lesion.
Figure 15A:
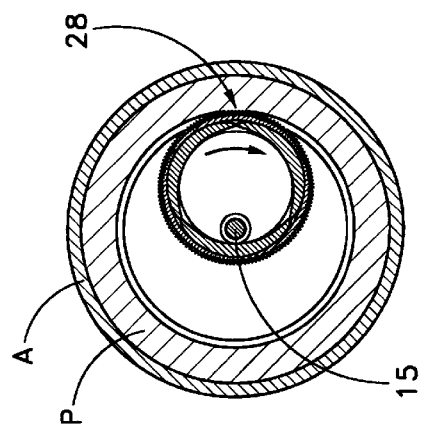
FIG. 15A is a transverse cross-sectional view of FIG. 13, taken along lines 15A—15A thereof.
Figure 15B:
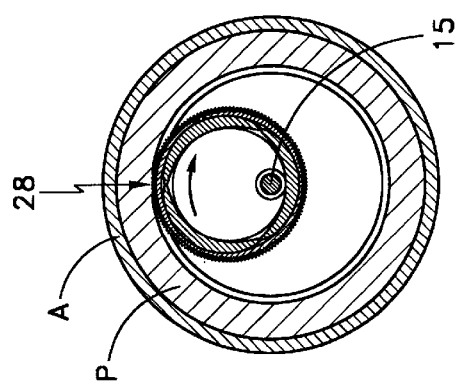
FIG. 15B is a transverse cross-sectional view similar to FIG. 15A, showing the rotating enlarged diameter section of the drive shaft in a moved position.
Figure 16A:
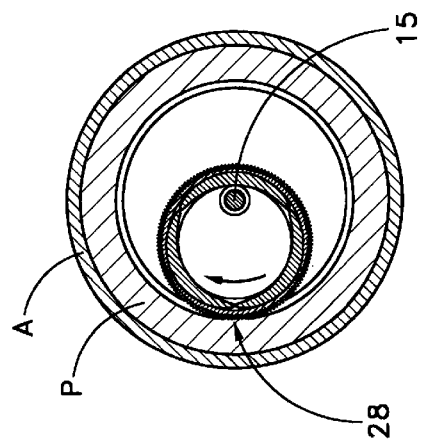
FIG. 16A is a transverse cross-sectional view of FIG. 14, taken along lines 16A—16A thereof.
Figure 16B:
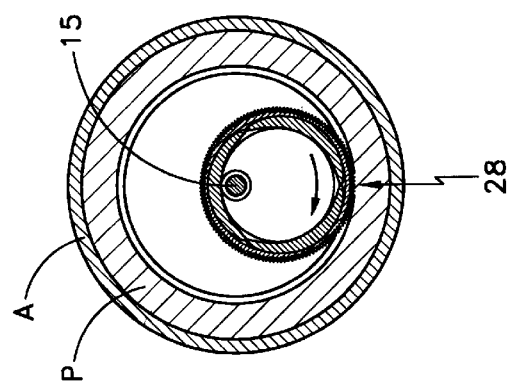
FIG. 16B is a transverse cross-sectional view similar to FIG. 16A, showing the rotating enlarged diameter section of the drive shaft in a moved position.

In FIGS. 5–6 the rotating eccentric enlarged diameter section 28 has been advanced over the guide wire 15 and is being advanced distally across a stenosis in an artery "A". The diameter of the stenosis (defined by plaque "P") is slightly smaller than the nominal maximum diameter of the eccentric enlarged diameter section 28 of the drive shaft 20, and, consequently, the eccentric enlarged diameter section 28 is removing a thin first layer of plaque "P." In FIG. 6 the eccentric enlarged diameter section 28 is shown advanced slightly distally and rotated 180° from the position shown in FIG. 5. As can be seen by comparing these two drawings, the plaque P generally centers the intermediate tissue removal section 35 of the eccentric enlarged diameter section 28 of the drive shaft within the stenosis. As the drive shaft 20 and the eccentric enlarged diameter section 28 rotate, the guide wire 15 is forced to revolve generally around the center of the stenosis. This movement is illustrated in further detail in FIGS. 7A–8B, which successively show the guide wire 15 revolving through the twelve o'clock, three o'clock, six o'clock and nine o'clock positions as the enlarged diameter section 28 of the drive shaft 20 makes a single rotation.

Figure 18:
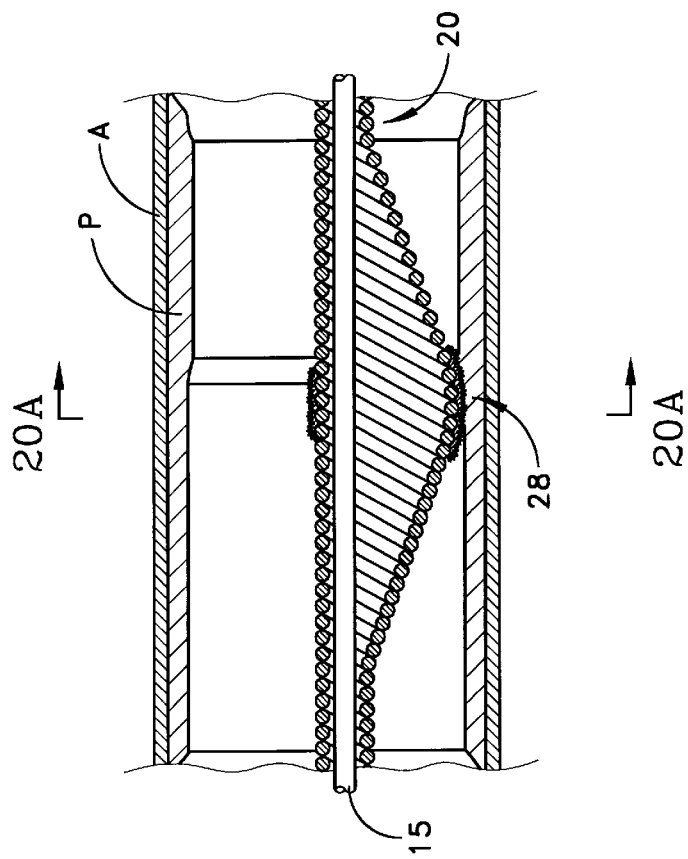
FIGS. 17–18 are longitudinal cross-sectional views similar to FIGS. 5–6 showing the rotating enlarged diameter section of the drive shaft being moved proximally across the stenotic lesion, which has now been almost entirely opened.
Figure 17:
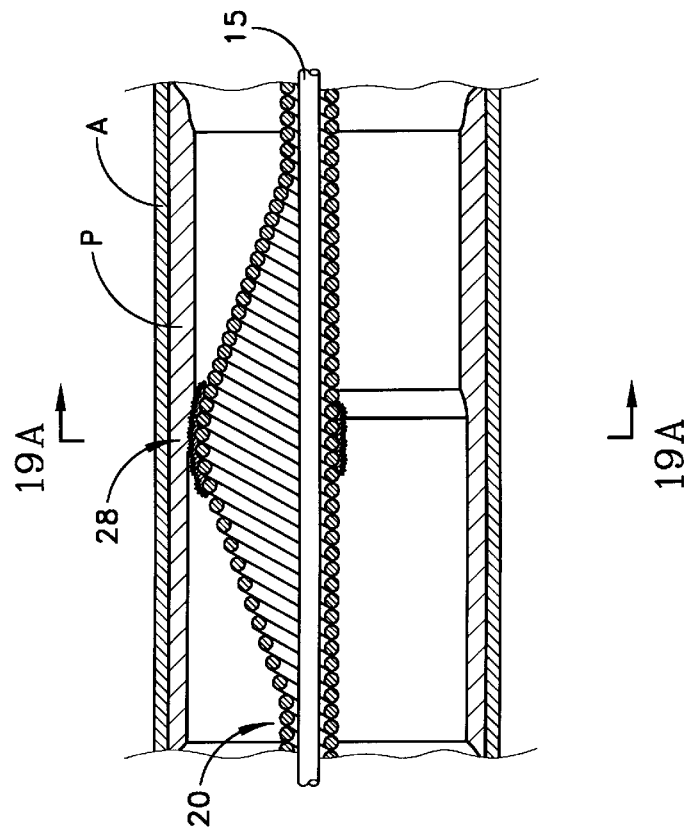

FIGS. 9–10 illustrate the rotating eccentric enlarged diameter section 28 being withdrawn proximally across the stenosis, which has now been partially opened. FIGS. 11A–12B show the guide wire 15 revolving through the six o'clock, nine o'clock, twelve o'clock and three o'clock positions as the enlarged diameter section of the drive shaft 20 makes a single rotation. Notice that the diameter of the circle through which the guide wire 15 revolves has decreased in proportion to the amount that the stenosis has been opened. FIGS. 13–14 show the rotating eccentric enlarged diameter section 28 being again advanced distally across the stenosis, which has now been opened further, and FIGS. 15A–16B show the movement of the enlarged diameter section 28 of the drive shaft 20 through a single rotation. At this stage of the procedure the stenosis has been opened sufficiently that rotation of the enlarged diameter section 28 within the stenosis no longer pushes the guide wire 15 through the circular motion. Thus, the position of the guide wire 15 remains constant in FIGS. 15A–16B. FIGS. 17–18 show the rotating eccentric enlarged diameter section 28 being withdrawn proximally across the stenosis, which has now been almost completely opened. As can be seen in these drawings and in FIGS. 19A–20B, the stenosis now has been opened to a diameter sufficiently large that the eccentric nature of the enlarged diameter section causes the guide wire 15 to revolve about the center of the stenosis.

Although FIGS. 5–20B illustrate the process of opening the stenosis in just a few steps, in actual practice it is preferable to remove the tissue relatively slowly, using numerous distal and proximal passes across the stenosis. Using the rotational atherectomy device of the invention the operator repeatedly moves the eccentric enlarged diameter section 28 distally and proximally through the stenosis. By changing the rotational speed of the device he is able to control the force with which the tissue removal surface is pressed against the stenotic tissue, thereby being able to better control the speed of the plaque removal as well as the particle size of tissue removed. Since the stenosis is being opened to a diameter larger than the nominal diameter of the enlarged diameter section, the cooling solution and the blood are able to constantly flow around the enlarged diameter section. Such constant flow of blood and cooling solution constantly flushes away removed tissue particles, thus providing more uniform release of removed particles than the Auth device referred to above.

The extent to which a stenosis in an artery can be opened to a diameter larger than the nominal diameter of the eccentric enlarged diameter section 28 depends on several parameters, including the shape of the eccentric enlarged diameter section 28, the mass of the eccentric enlarged diameter section 28, the distribution of that mass and, therefore, the location of the center of mass of this section with respect to the rotational axis of the drive shaft, and the speed of rotation. The speed of rotation is a significant factor in determining the centrifugal force with which the tissue removing surface of the enlarged diameter section is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Helically wound multifilar drive shafts with eccentric enlarged diameter sections may be manufactured in accordance with the following methods of the invention.

Figure 21:
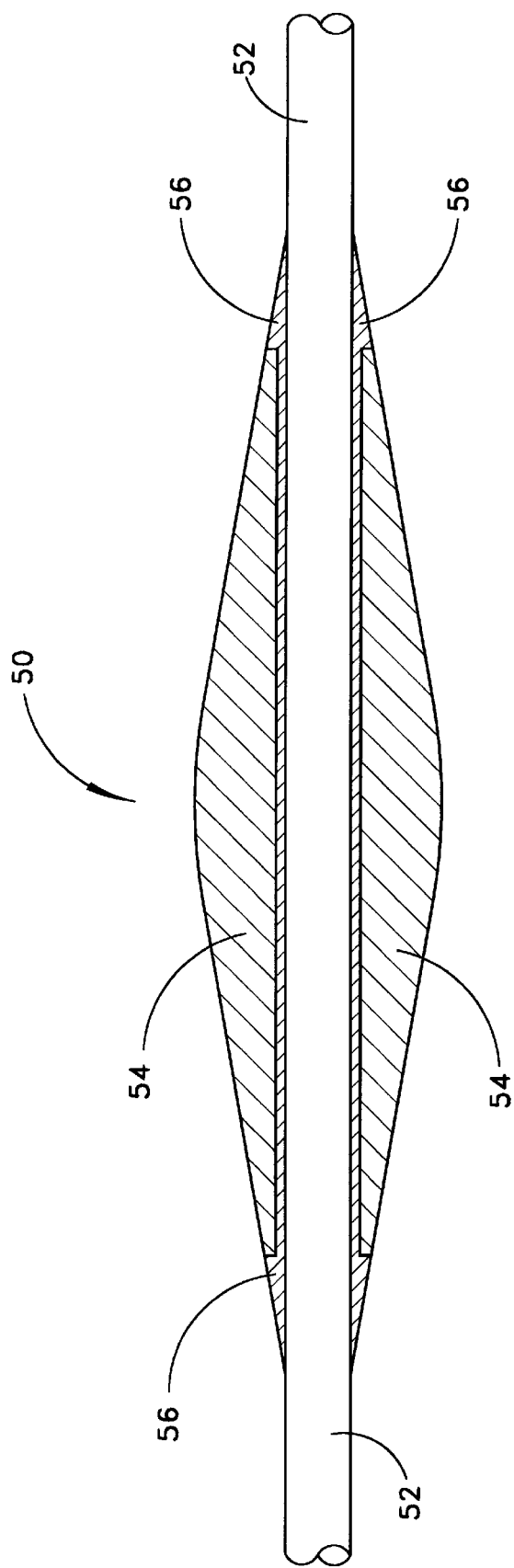
FIG. 21 is a longitudinal cross-sectional view of the enlarged diameter section of a mandrel used in manufacturing an eccentric rotational atherectomy device of the invention.
Figure 22:
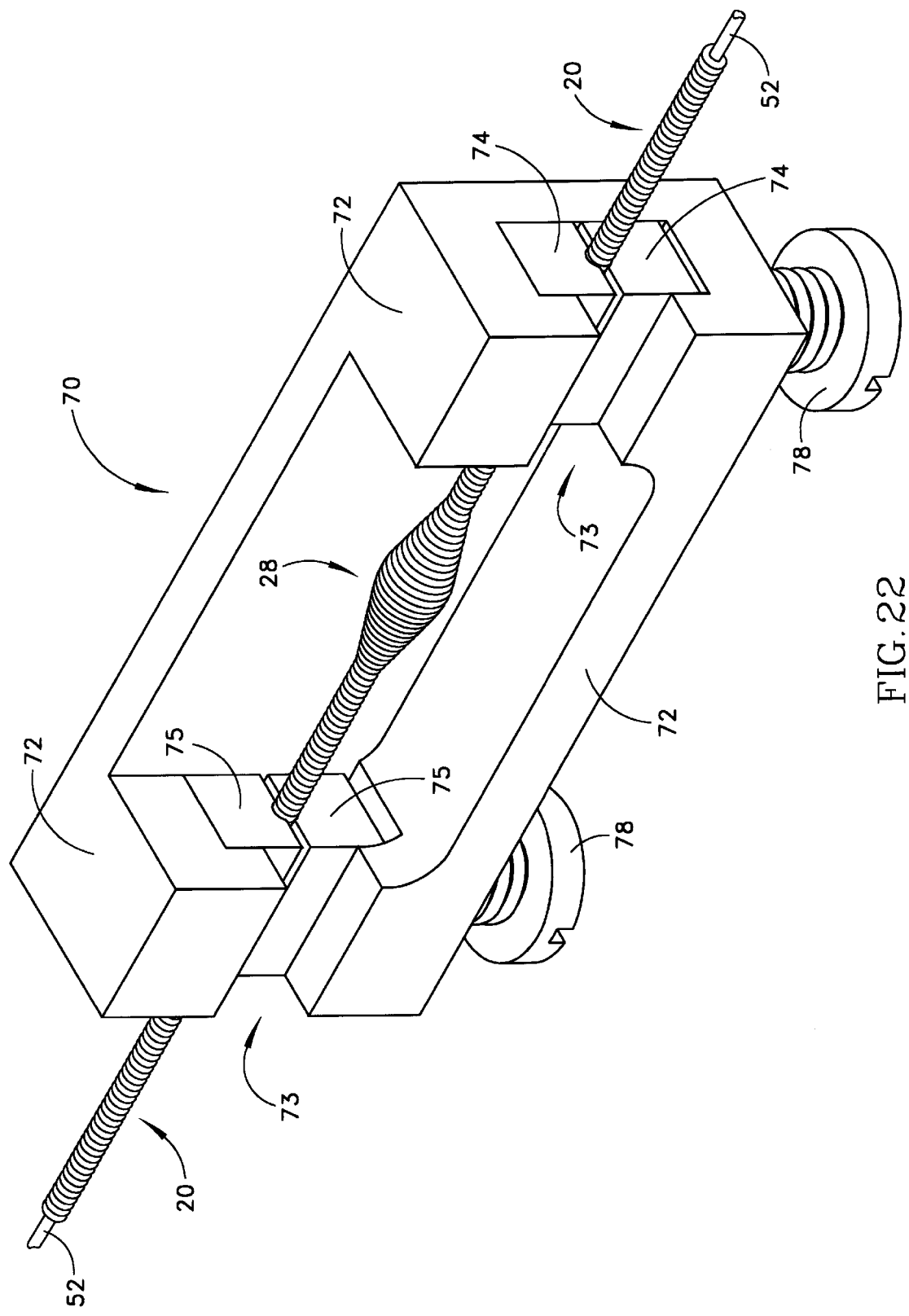
FIG. 22 is a perspective view of a clamp used in an initial step in the process of manufacturing an eccentric atherectomy device of the invention.
Figure 26:
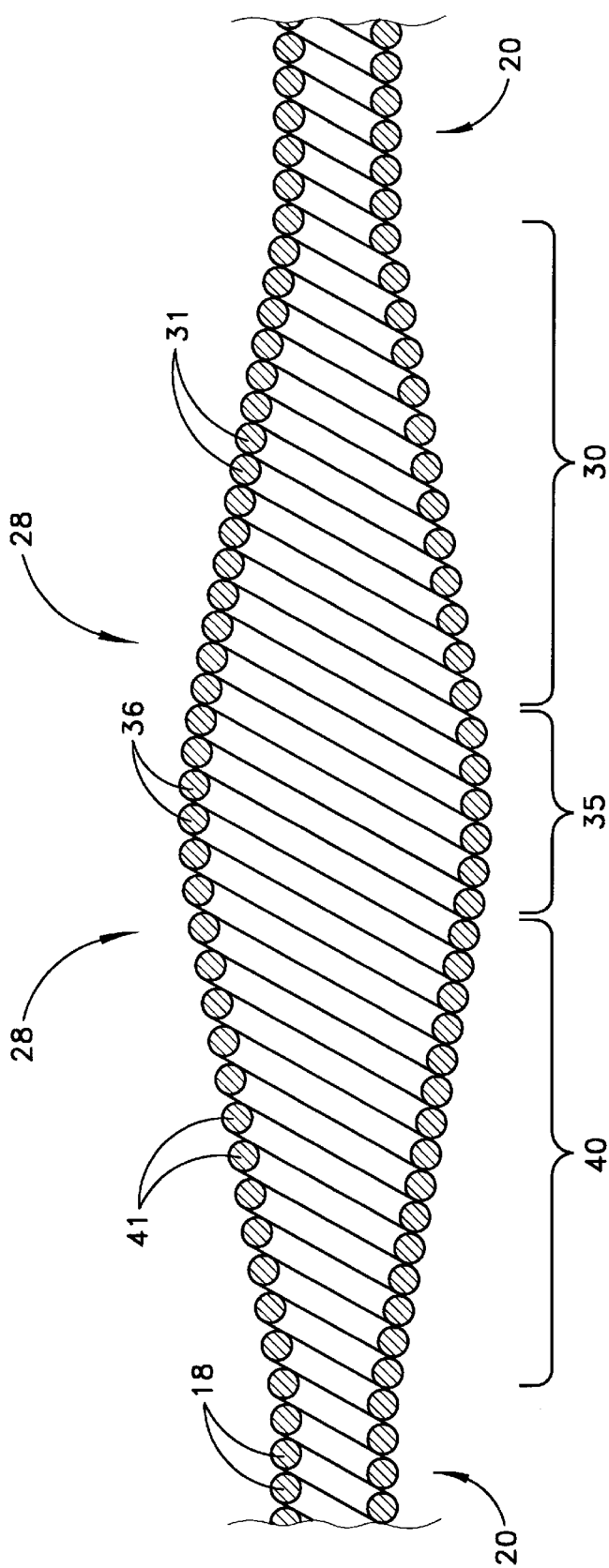
FIG. 26 is a longitudinal cross-sectional view of the enlarged diameter section of a drive shaft produced using the mandrel and clamp shown in FIGS. 21–25.

One method of the invention is illustrated in FIGS. 21–27A, and includes the use of a mandrel about which suitable wires may be wound. FIG. 21 depicts a mandrel 50 having a generally symmetrical enlarged diameter section. The mandrel 50 includes a mandrel shaft 52 having a generally constant diameter along its entire length. A generally symmetrical enlarged diameter component 54 is secured to the mandrel shaft 52 by a suitable bonding material such as solder 56. The solder joint may be machined or sanded to achieve a smooth transition between the symmetrical enlarged diameter component 54 and the mandrel shaft 52.

After the mandrel 50 is so constructed, suitable wires may be wound about the mandrel 50, including both the mandrel shaft 52 and the symmetrical enlarged diameter component 54. Before the winding tension on the wires has been released, a clamp 70 (shown in FIGS. 22–25) is secured on the drive shaft straddling the enlarged diameter section. The clamp includes a clamp frame 72 with a slot 73, two sets of clamping blocks 74 and 75, and a pair of set screws 78. Fixation of the clamp on the drive shaft is accomplished by first passing the drive shaft through the slot 73 in the clamp frame 72, next positioning the clamping blocks 74 and 75 about the drive shaft 20 and moving them into the clamp frame 72, and finally tightening set screws 78 to firmly clench the drive shaft with its symmetrical enlarged diameter section between the clamping blocks 74 and 75. Once the set screws 78 are tightened, the winding tension on the drive shaft wires may be released. Those portions of the drive shaft wires not captured by the clamp will unwind to a diameter slightly larger than the mandrel, but the clamp will prevent such unwinding for the entire portion of the drive shaft located between the two sets of clamping blocks 74 and 75. Clamping blocks 74 and 75 preferably are made from a relatively soft metal such as nickel.

FIG. 23 illustrates in longitudinal cross-section how the drive shaft 20 is clenched by clamping blocks 74 and 75. In FIGS. 23 and 24 the portions of the drive shaft not captured by the clamp are shown as having unwound to a diameter larger than the diameter of the portion captured by the clamp. FIGS. 23 and 24 however, significantly exaggerate the degree of unwinding—typically the outer diameter of the drive shaft, as a result of unwinding, will increase by only about 2–10%.

Once the clamp 70 has been secured to the drive shaft and the portions of the drive shaft not captured by the clamp 70 are allowed to unwind to a slightly larger diameter, then the distal length of the drive shaft, together with the clamp 70, is heat treated to give the wires of the drive shaft the desired "set" in the generally symmetrical shape. Only the distal length of the drive shaft, including the section of the drive shaft which is distal to the enlarged diameter section, the enlarged diameter section itself, and about 80 mm of the drive shaft's length proximal to the enlarged diameter section need be placed in the heat treatment oven.

Desirably the heat treatment is in the range of about 230° C. to about 600° C. for at least about 10 minutes. At lower temperatures the heat treatment will need to be longer than at higher temperatures. Preferably the heat treatment is conducted at a temperature of between about 360° C. and about 600° C. for at least about a half hour, and most preferably between about 540° C. and about 580° C. for at least about half an hour. Applicants have obtained good results with this heat treatment at a temperature of about 560° C. for about one hour. The particular temperature and time selected may vary depending on the maximum diameter of the enlarged diameter section and on the cross-sectional diameter of the wire. Applicants have successfully used stainless steel wire with a diameter of about 0.006 inches for drive shafts having eccentric enlarged diameter sections with diameters of up to about 2 mm. Applicants have successfully used type 304 stainless steel wire available from Fort Wayne Metals Research Products Corp. (Fort Wayne, Ind.) under the name "Hyten." Preferably the wire has a tensile strength of about 445±10 ksi.

Preferably the heat treatment is conducted in an inert gas environment, utilizing, e.g., argon, SF6 or any other suitable inert gas. Good results have been obtained using an argon flow rate of 0.055 scfm in a heated chamber with internal dimensions of approximately 15 cm×15 cm×2 cm. The chamber may be heated in any convenient way, such as by placing it in an oven.

After this heat treatment has been completed and both the drive shaft 20 and the clamp 70 have cooled, the drive shaft is removed from the clamp. The mandrel 50 must then be removed from the drive shaft. Applicants have found that the mandrel 50 may be removed by constructing the components of the mandrel 50 from materials different from the drive shaft wire so that the mandrel components may be dissolved in appropriate solutions which do not materially adversely affect the drive shaft itself. For example, the mandrel shaft 52 may be made from high carbon steel, the enlarged diameter portion 54 from brass (e.g., round brass rod sold by Vincent Metals, of Minneapolis, Minn. as "low leaded" brass rod comprised of 62.0% copper, 36.2% zinc and 1.8% lead, or "high speed—free cutting" brass rod comprised of 61.5% copper, 35.5% zinc and 3.0% lead), the solder securing the enlarged diameter portion 54 to the mandrel shaft 52 from a composition of 61% tin and 39% lead, and the helically wound wire from the "Hyten" stainless steel wire mentioned above. (Preferably the flux used in soldering the enlarged diameter component 54 to the mandrel shaft 52 is comprised of 75% $ZnCl_2$ and 25% $NH_4Cl$, these compounds being dissolved in distilled water at maximum concentration (i.e., creating a saturated solution)).

Preferably the mandrel is removed in two steps. First, the mandrel shaft is removed by immersing the entire drive shaft, together with the mandrel 50, in an acidic solution. Preferably the acidic solution is a solution of nitric acid (at least about a 10% solution, and preferably about a 15% solution). Desirably the nitric acid is at a temperature of about 80–100° C. This first immersion preferably lasts at least about four hours, and preferably for about 8–10 hours until the mandrel shaft 52 is completely dissolved. Applicants have found that the process of dissolving the mandrel shaft 52 usually is completed when gas bubbles stop rising to the surface of the nitric acid. As with the heat treatment process described above, preferably the drive shaft is kept generally straight when immersed in the hot nitric acid. Alternately, the drive shaft may be coiled, but, in that event, the diameter of the coil preferably should be not less than about seven or eight inches, because the heat of this process can also affect the shape of the drive shaft.

After the mandrel shaft 52 has been dissolved, the distal portion of the drive shaft, together with the enlarged diameter portion 54 of the mandrel (which has not yet been dissolved), and preferably including at least a short section of the drive shaft proximal to the enlarged diameter section, is immersed in a more concentrated acidic solution. Again, preferably the acidic solution is a solution of hot nitric acid. Typically the nitric acid concentration is between about 30% and about 40% (preferably about 35%), and the temperature is at least about 50° C. (preferably about 80–100° C.). This immersion desirably is conducted for at least about four hours, and preferably about 8–10 hours, to dissolve the enlarged diameter portion 54 of the mandrel and the solder 56.

Immediately after removing the drive shaft from this second immersion into nitric acid the drive shaft is washed for several minutes in running water. The drive shaft then is placed into boiling distilled water for 15–20 minutes, and then dipped into 96% alcohol and air dried or wiped with a clean cloth. At this stage in the process the drive shaft 20 has an enlarged diameter section 28 with the generally symmetrical shape shown in FIG. 26.

Figure 27:
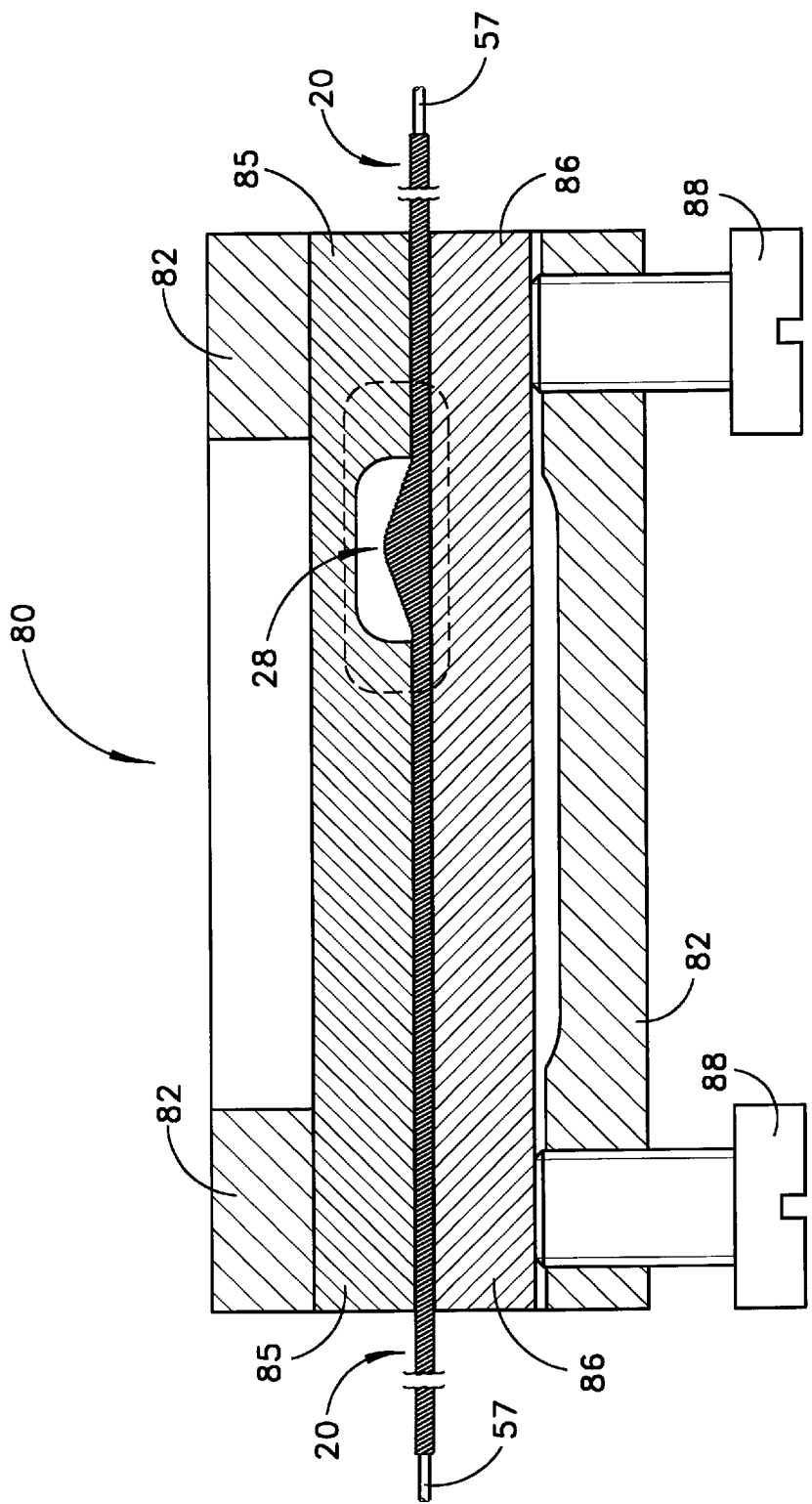
FIG. 27 is a longitudinal cross-sectional view of a second clamp used in a subsequent step in the process of manufacturing an eccentric atherectomy device of the invention.
Figure 27A:
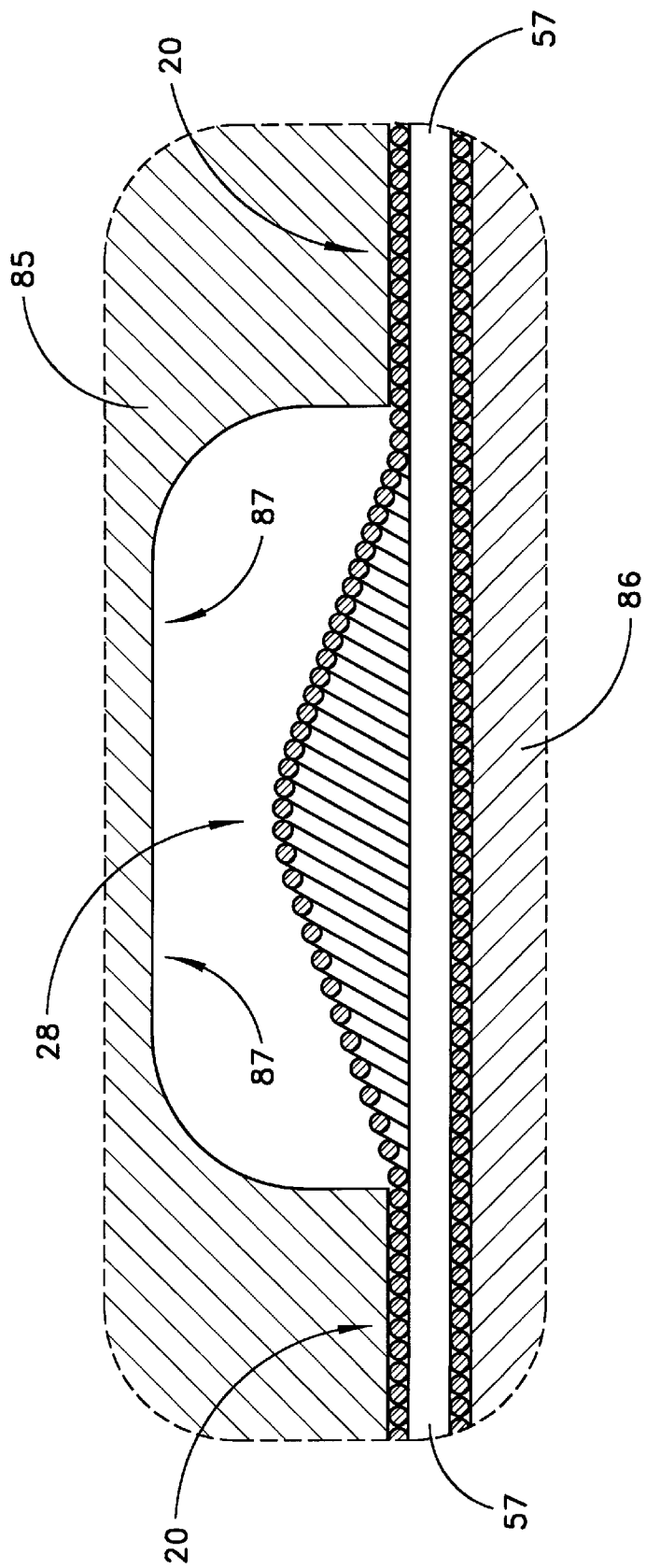
FIG. 27A is an enlarged view showing in longitudinal cross-section details of a portion of FIG. 27.

FIGS. 27–27A illustrate the next step in the process, which gives the enlarged diameter section 28 its asymmetric shape. A second clamp 80 is secured on the drive shaft straddling the enlarged diameter section 28. The clamp includes a clamp frame 82 similar to the frame 72 of the first clamp 70 (see FIGS. 22–25), a single set of clamping blocks 85 and 86, and a pair of set screws 88. Fixation of the second clamp 80 on the drive shaft is accomplished in similar fashion to fixation of the first clamp 70, as described above. The second clamp 80 differs from the first clamp in that the clamping blocks 85 and 86 force the enlarged diameter section 28 into the asymmetrical shape described above. For this purpose, the lower clamping block 86 is longitudinally flat, and the upper clamping block 85 includes a recess 87 (see FIG. 27A) permitting the enlarged diameter section 28 to be formed into the desired shape. Preferably a support wire 57 is placed within the lumen of the drive shaft 20 to provide some stiffness to the drive shaft during this part of the manufacturing process, and to help assure that the enlarged diameter section 28 is formed into the desired shape. The wire 57 also supports the portions of the drive shaft outside of the clamp, preventing them from being bent inadvertently.

Once the second clamp 80 has been secured to the drive shaft 20 then the distal length of the drive shaft, together with the clamp 80, is heat treated a second time to give the wires of the drive shaft 20 a "set" in the desired asymmetrical shape. Only the distal length of the drive shaft 20, including the section of the drive shaft which is distal to the enlarged diameter section 28, the enlarged diameter section 28 itself, and about 80 mm of the drive shaft's length proximal to the enlarged diameter section 28 need be placed in the heat treatment oven.

Desirably this second heat treatment is in the range of about 230° C. to about 600° C. for at least about 10 minutes. At lower temperatures the heat treatment will need to be longer than at higher temperatures. Preferably the heat treatment is conducted at a temperature of between about 360° C. and about 600° C. for at least about a half hour, and most preferably between about 470° C. and about 530° C. for at least about half an hour. Applicants have obtained good results with this heat treatment at a temperature of about 500° C. for about one hour. As with the first heat treatment, the particular temperature and time selected may vary depending on the maximum diameter of the enlarged diameter section and on the cross-sectional diameter of the wire. Preferably the second heat treatment is also conducted in an inert gas environment. Preferably both the inert gas of choice and its flow rate, as well as the fixtures used during the second heat treatment are the same as are used in the first heat treatment.

Following the second heat treatment (or at any time after the wires have been wound onto the mandrel) desirably the entire drive shaft is heat treated at a temperature of between about 200° C. and about 400° C. (and preferably between about 250° C. and about 350° C.) for at least about ten minutes (and preferably for at least about half an hour). Applicants have achieved good results with this heat treatment at a temperature of about 300° for about an hour. This heat treatment relieves stress in the wire turns of the drive shaft. The drive shaft 20 then is finished by electropolishing and application of the abrasive material 24 to create the tissue removing segment of the drive shaft (as described above).

FIGS. 28–31 illustrate yet a modified process of the invention which facilitates the manufacture of a drive shaft having spaces between wire turns of the asymmetric enlarged diameter section 28. These spaces permit the abrasive particle bonding material 26 to be applied to the wire turns without securing the wire turns to each other. In this method the second clamp 90 includes a clamp frame 92 similar to the frames of the clamps described above, a pair of set screws 98, and a set of slightly modified clamping blocks 95, 96 and 97. The clamping blocks differ from the above-described clamp in that the upper block 85 is replaced by two upper clamping blocks 95 and 96, the significance of which will be described below.

Figure 28:
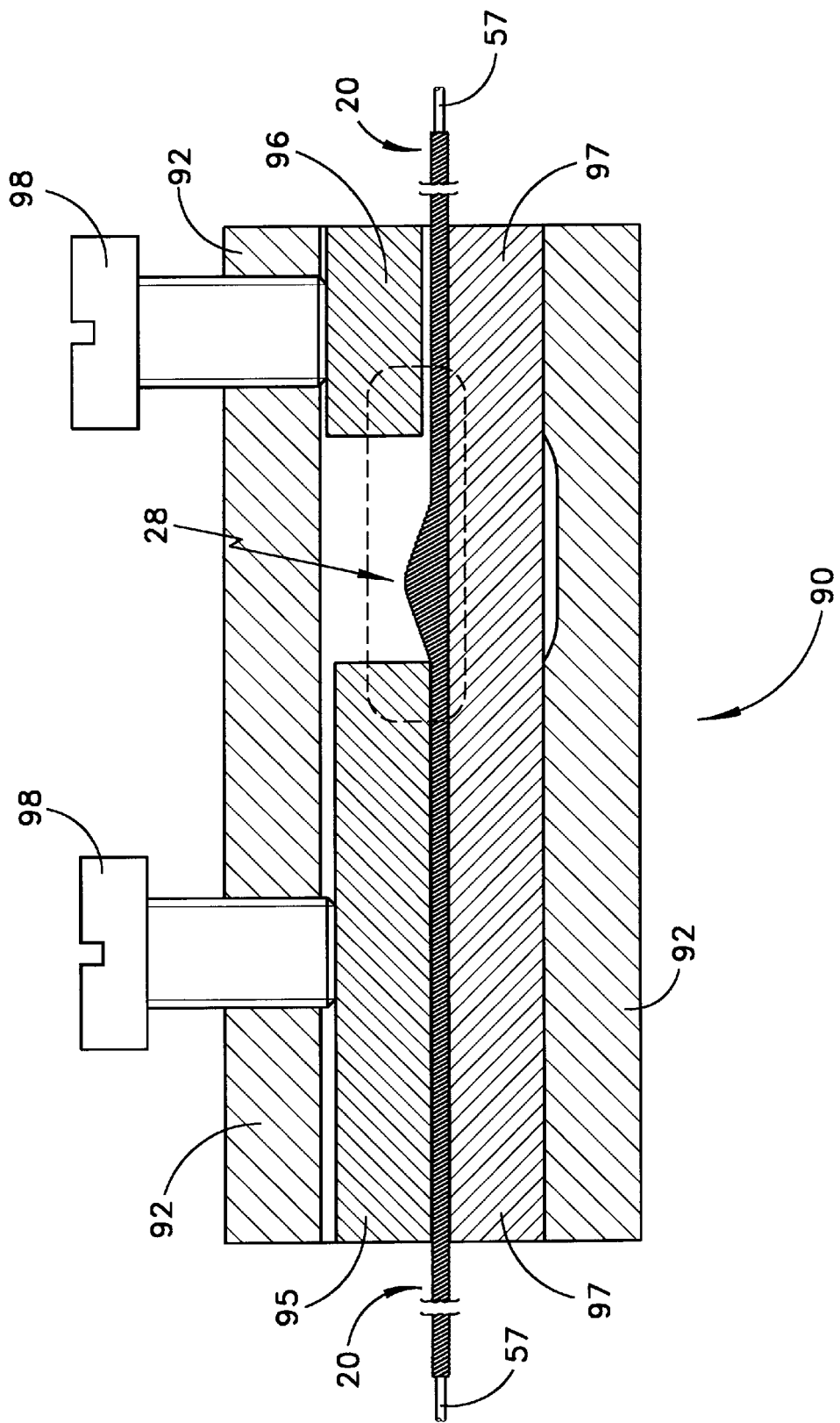
FIG. 28 is a longitudinal cross-sectional view of a modified version of the clamp shown in FIG. 27, the clamp of FIG. 28 having discrete clamping blocks proximally and distally of the enlarged diameter section of the drive shaft so that the enlarged diameter section can be stretched after the drive shaft is secured within the clamp by one of the clamping blocks.
Figure 28A:
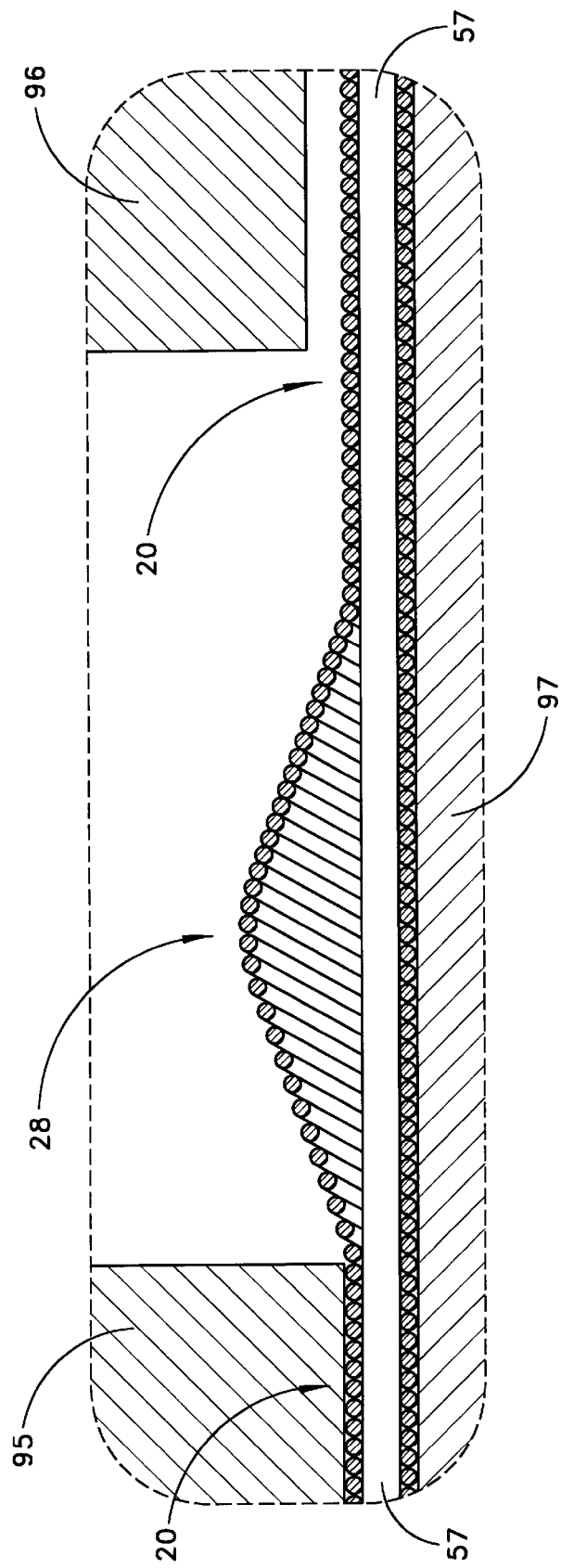
FIG. 28A is an enlarged view showing in longitudinal cross-section details of a portion of FIG. 28.
Figure 29:
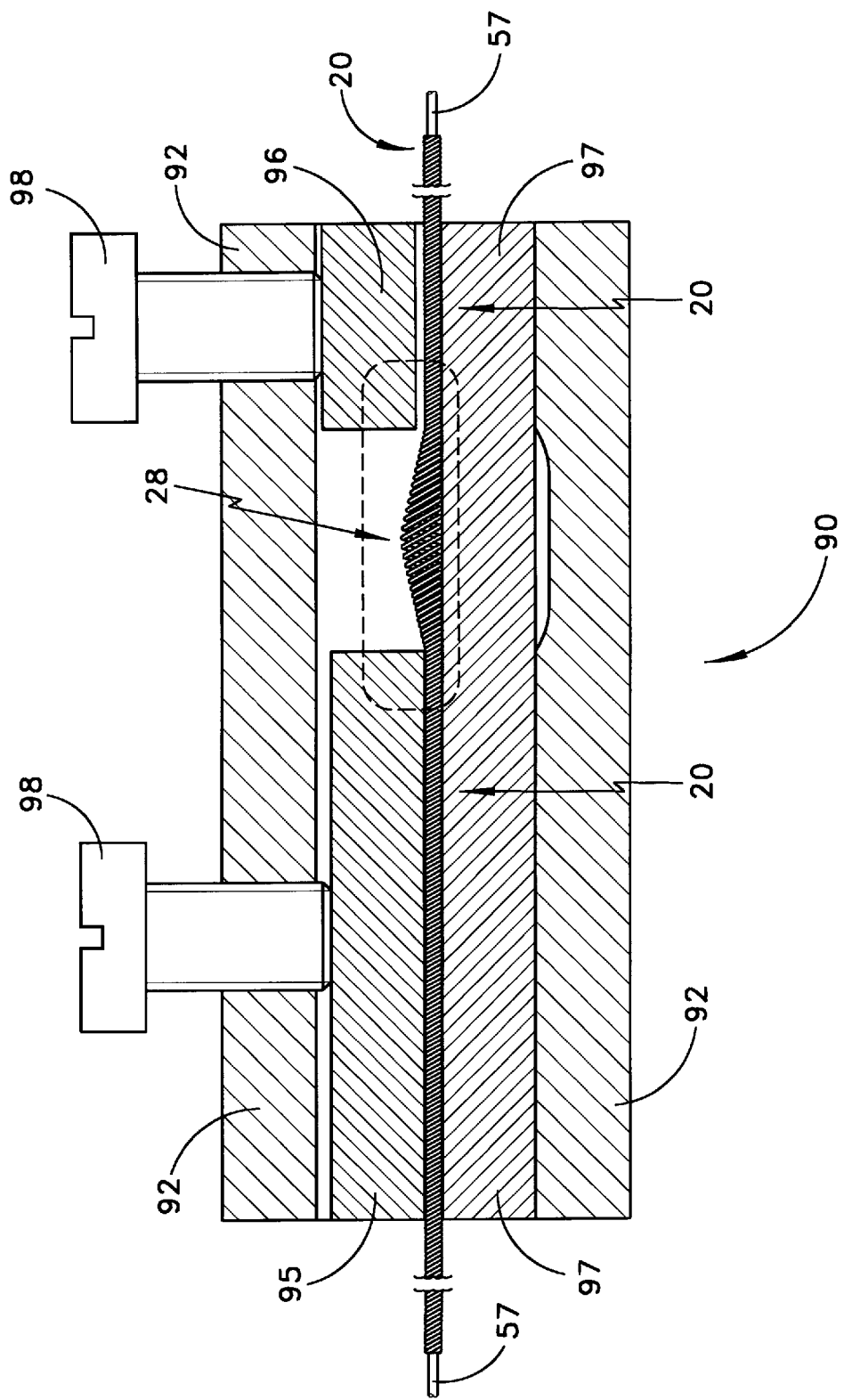
FIG. 29 is a longitudinal cross-sectional view of the clamp shown in FIG. 28 with the enlarged diameter section of the drive shaft in a stretched position.
Figure 29A:
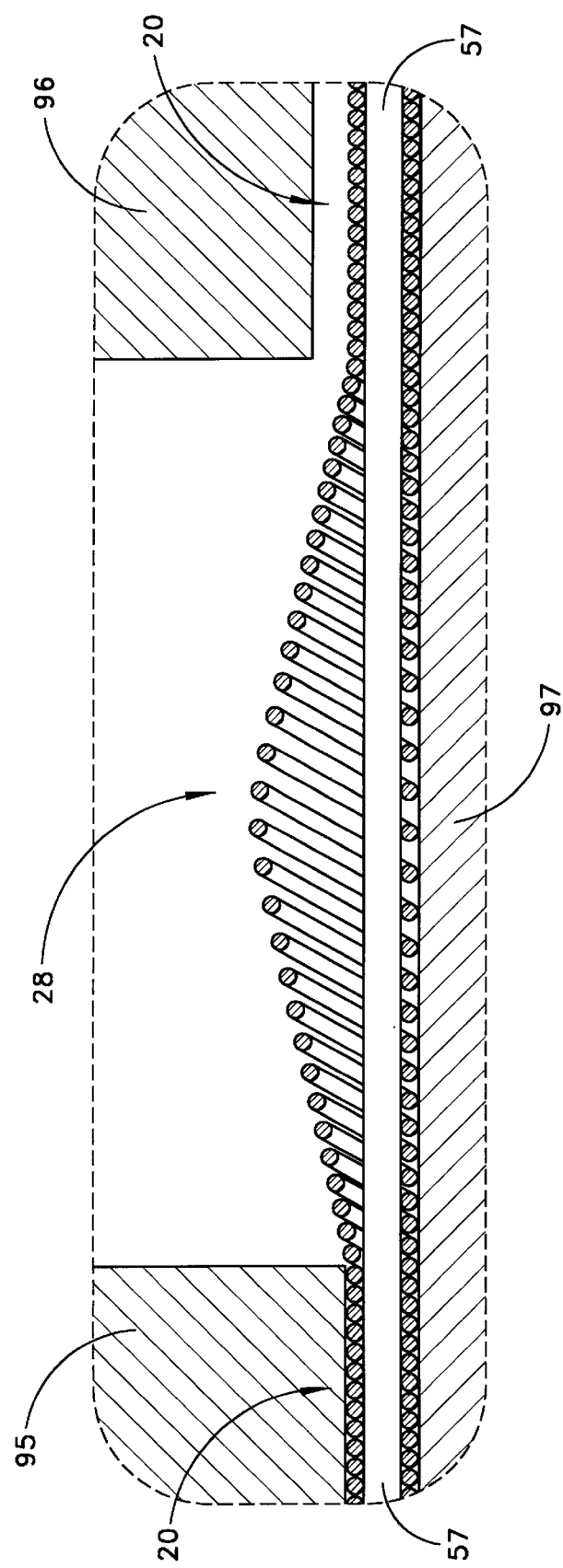
FIG. 29A is an enlarged view showing in longitudinal cross-section details of a portion of FIG. 29.

In FIGS. 28–28A the left set screw 98 has been tightened to secure the proximal portion of the drive shaft 20 between upper clamping block 95 and the elongated lower clamping block 97. In FIGS. 29–29A the portion of the drive shaft distal to the proximal clamping block 95 has been elastically stretched longitudinally, creating spaces between some of the wire turns of the enlarged diameter section 28. Such separation will be most significant among the largest diameter wire turns of the drive shaft. The amount of separation of the wire turns can be calculated using the formula $\lambda=(8FD^3)/Gd^4$, where $\lambda$ is the coil pitch (measured center-to-center from one wire turn to the next), F is the stretching force applied to the wire coil, D is the diameter of the wire turns, d is the cross-sectional diameter of the wire, and G is a coefficient specific to the metal from which the wire is made. As one can see from this formula, the increase in coil pitch $\lambda$ in as a function of the stretching force is proportional to the cube of the diameter of the wire turns.

Figure 30:
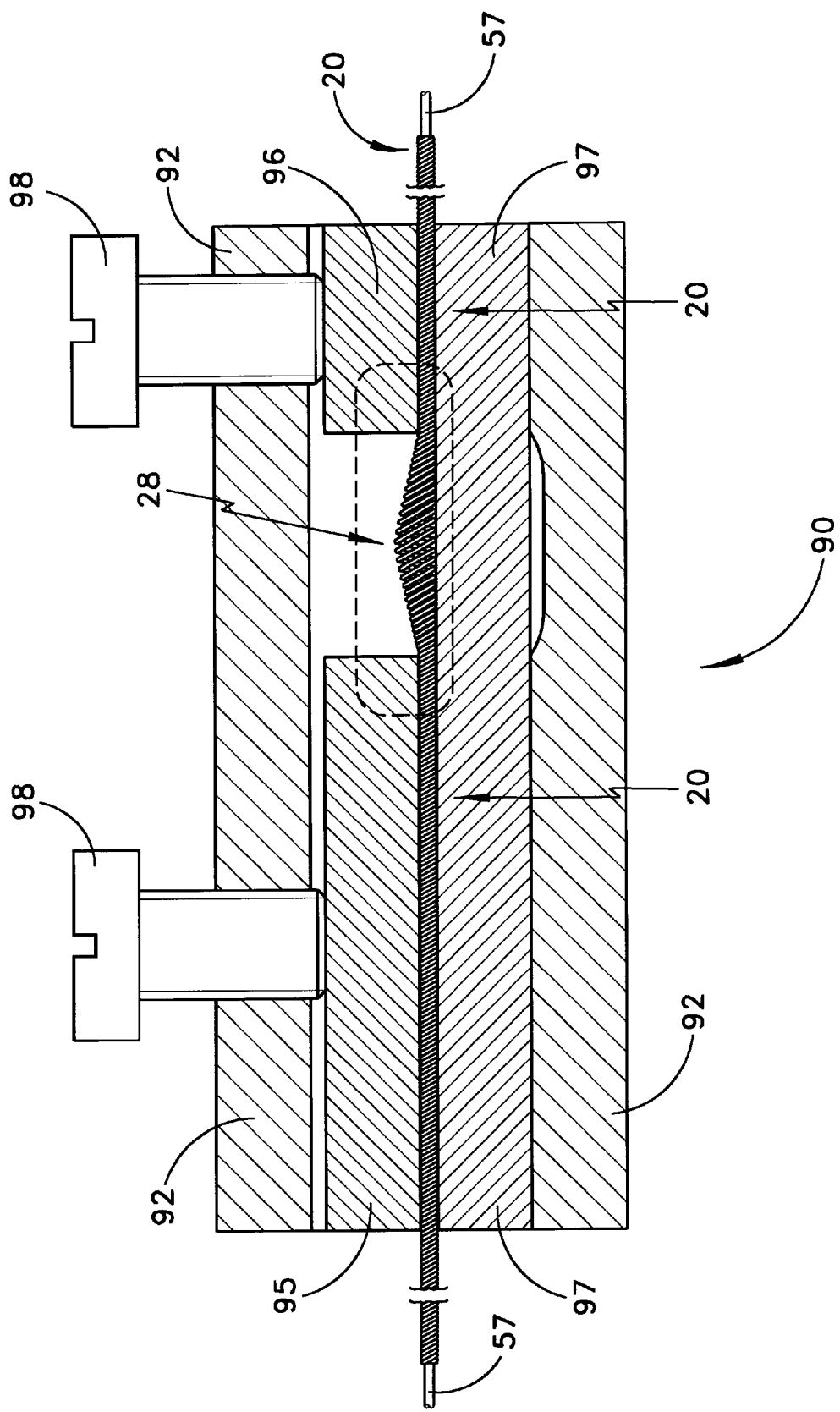
FIG. 30 is a longitudinal cross-sectional view of the clamp shown in FIGS. 28–29 after both the proximal and distal clamping blocks have been tightened to secure the drive shaft within the clamp with the enlarged diameter section in its stretched position.
Figure 30A:
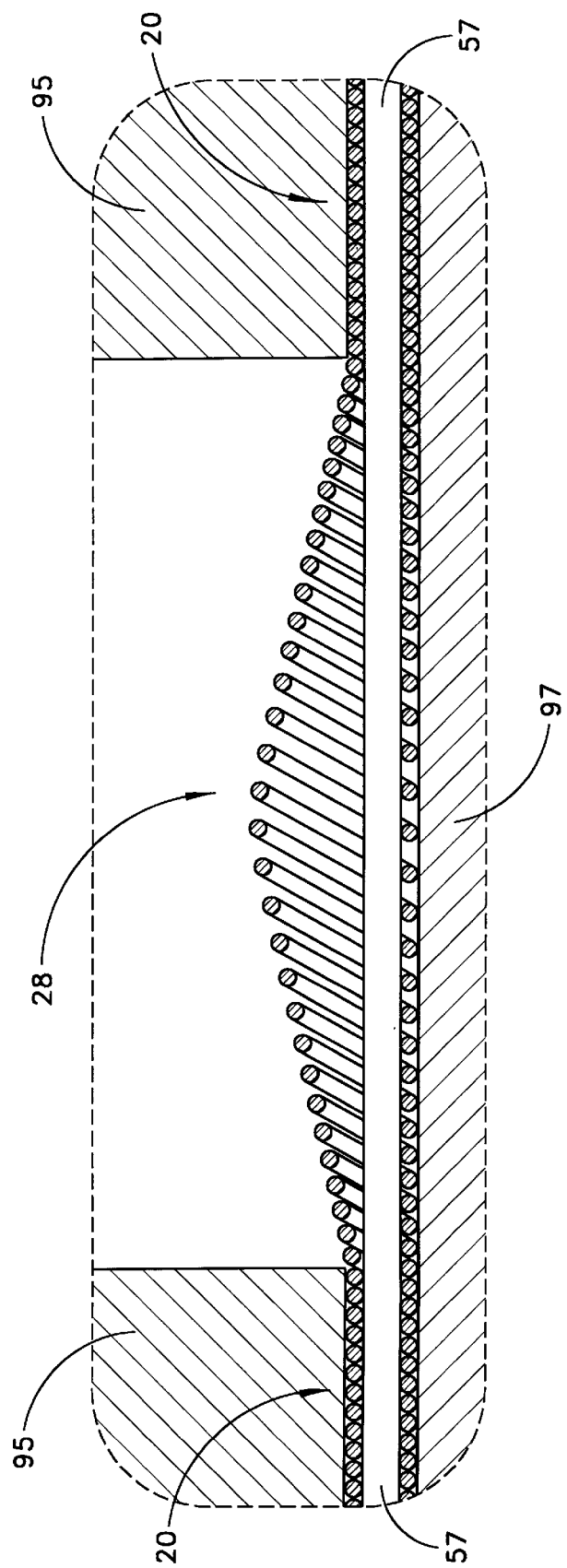
FIG. 30A is an enlarged view showing in longitudinal cross-section details of a portion of FIG. 30.

In FIGS. 30–30A the right set screw 98 has been tightened to secure the other upper clamping block 96, thus holding the enlarged diameter section 28 in its elastically stretched position. At this stage the enlarged diameter section 28 is ready for the second heat treatment, as described above, thereby giving the wire turns of the enlarged diameter tissue removal section 28 a set in the stretched, asymmetric position.

Figure 31:
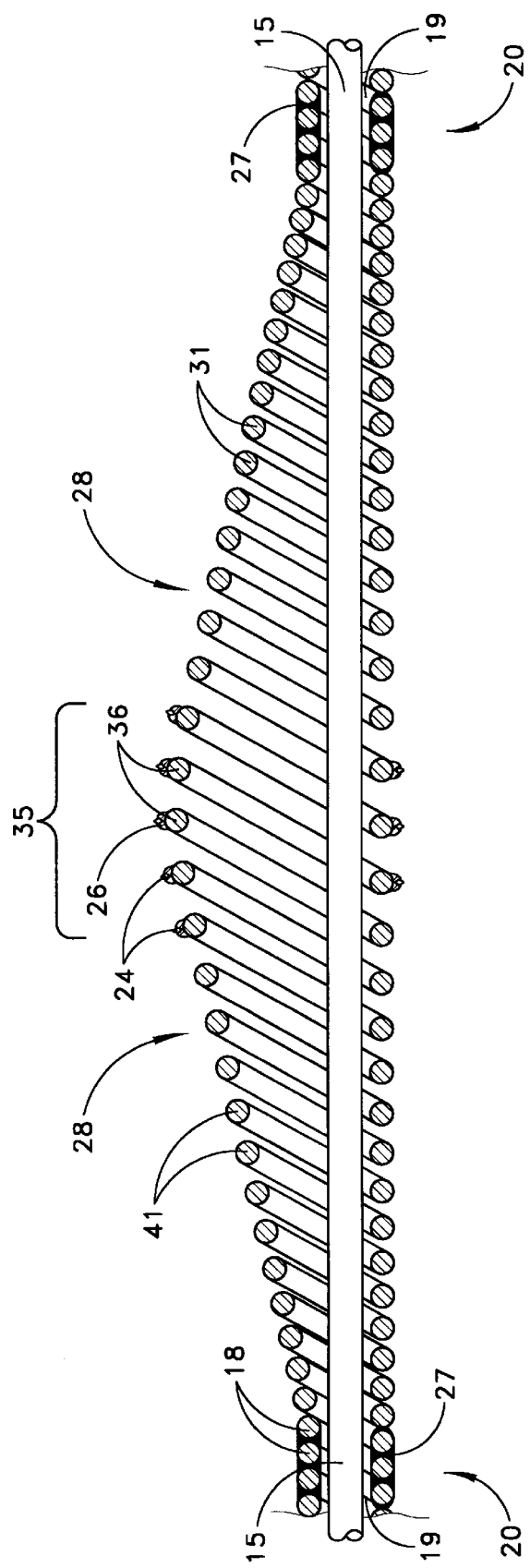
FIG. 31 is a longitudinal cross-sectional view of the enlarged diameter section of a drive shaft produced using the clamp shown in FIGS. 28–30.

FIG. 31 shows the resultant enlarged diameter section 28 after the remaining processing has been completed, including attachment of abrasive particles 24 to the wire turns 36 of the intermediate portion 35 by a suitable bonding material 26. Because the bonding material 26 does not attach adjacent wire turns to each other, the enlarged diameter section is extremely flexible, and able to navigate relatively tight turns in an artery.

As depicted in FIG. 31, radio-opaque markers 27, made from gold, platinum, iridium, alloys of these metals or other suitable radio-opaque materials, may be placed just distal and just proximal of the enlarged diameter section 28. These markers also serve to secure several wire turns of the drive shaft to each other just distal and just proximal to the enlarged diameter section of the drive shaft.

Figure 32:
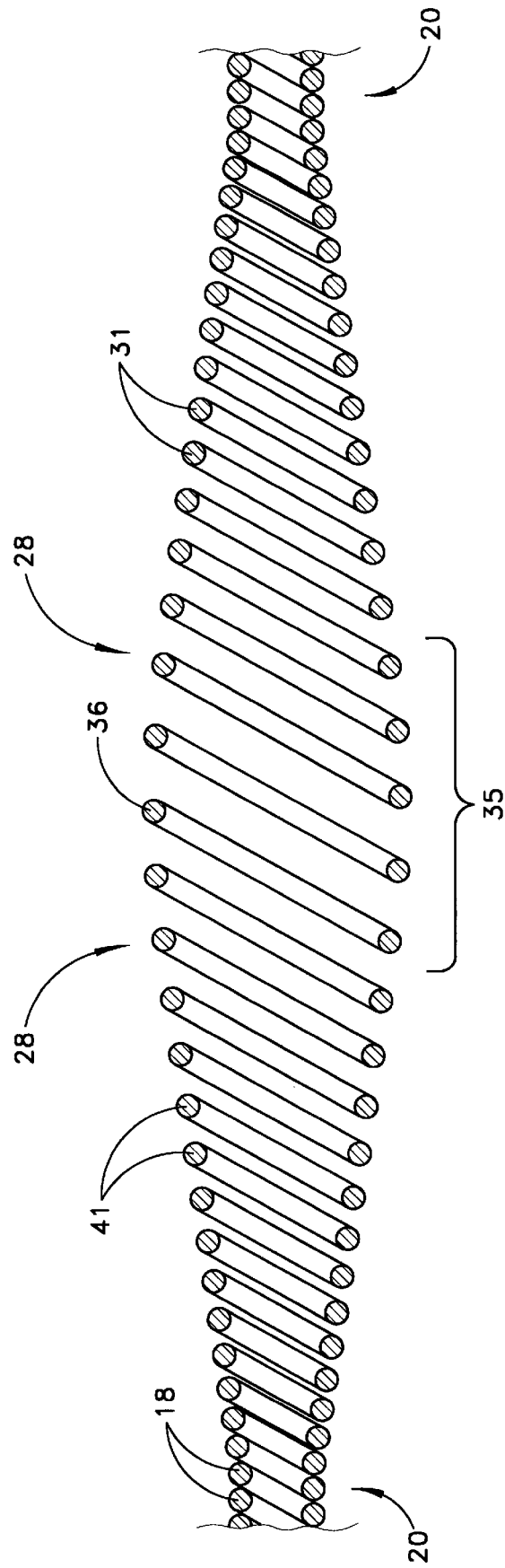
FIG. 32 illustrates how the gaps between adjacent wire turns of the enlarged diameter tissue removal section may be formed by inelastically stretching the enlarged diameter section.
Figure 33:
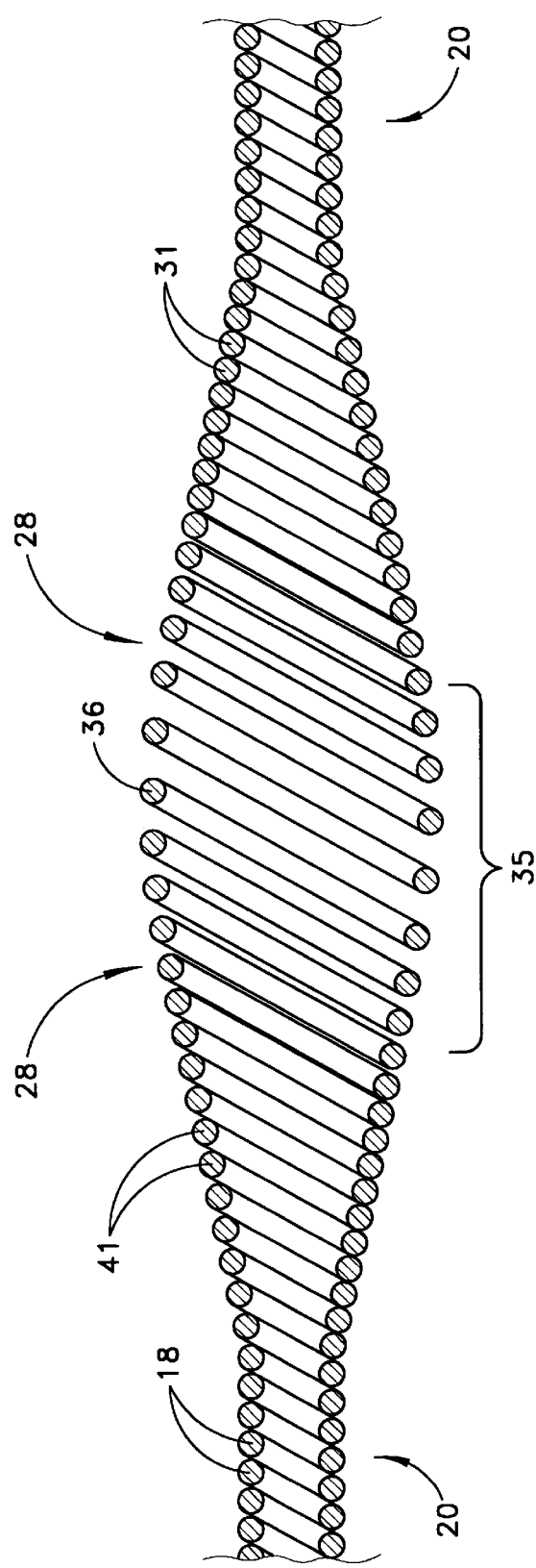
FIG. 33 is a longitudinal cross-sectional view of the enlarged diameter section of FIG. 32 after the stretching force has been released, the inelastically stretched wire turns remaining spaced from each other.

FIGS. 32–33 illustrate another method of stretching the enlarged diameter tissue removal section 28 to create gaps between adjacent wire turns. In this method, the enlarged diameter section 28 is longitudinally stretched sufficiently to inelastically deform at least an intermediate portion 35 of the enlarged diameter section, thereby creating spaces between the wire turns of the middle portion of the enlarged diameter tissue removal section. FIG. 32 shows the a symmetrical enlarged diameter section 28 in this inelastically stretched position. In FIG. 33, the longitudinal stretching force has been removed, allowing the wire turns to elastically recoil. Permanent gaps have been formed in the intermediate (middle) portion 35 of the enlarged diameter section 28, while the proximal and distal portions of the enlarged diameter section have elastically recovered their original shape.

Figure 34:
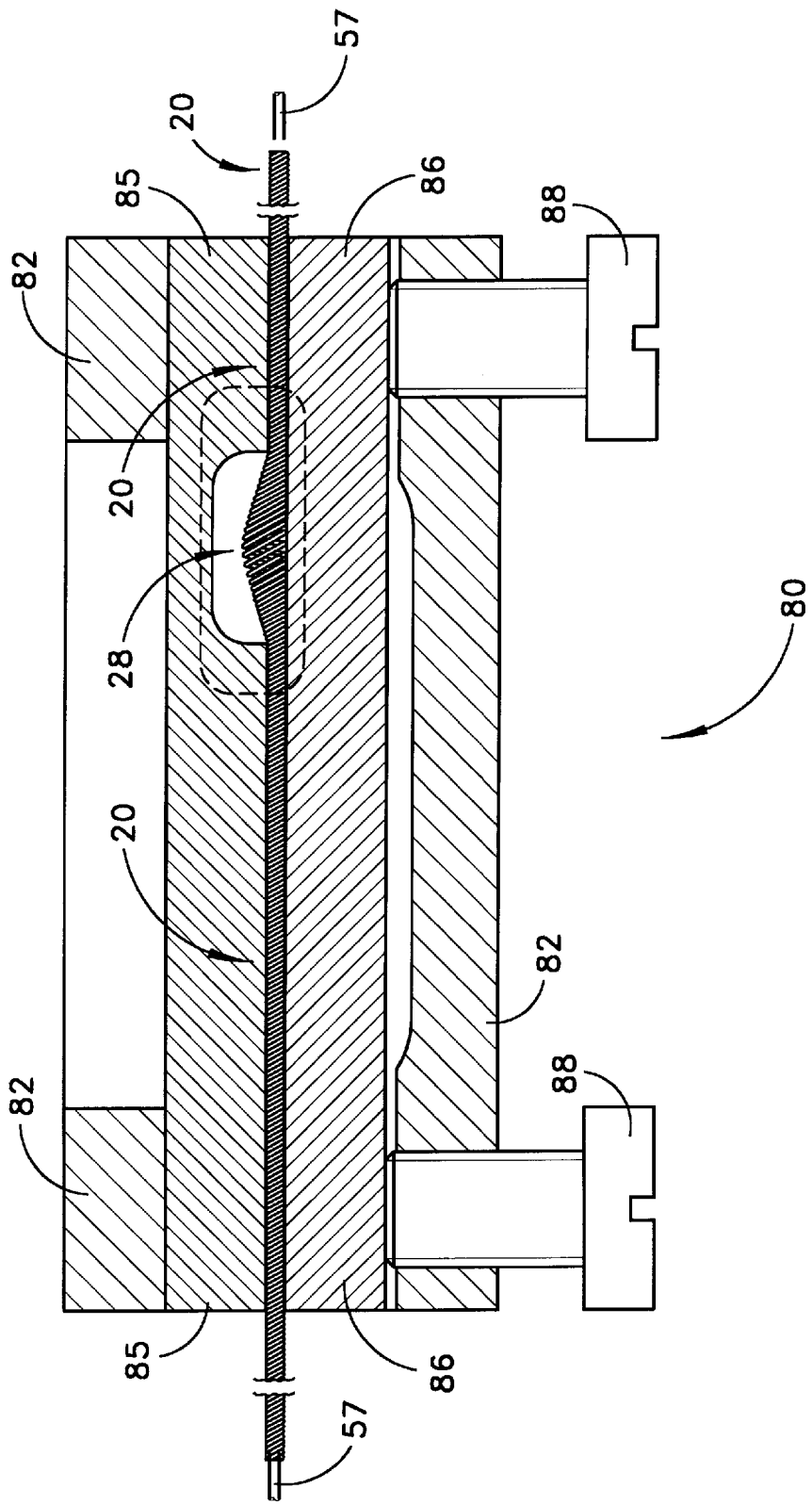
FIG. 34 illustrates the drive shaft of FIG. 33 placed in a clamp of the type shown in FIG. 27.
Figure 34A:
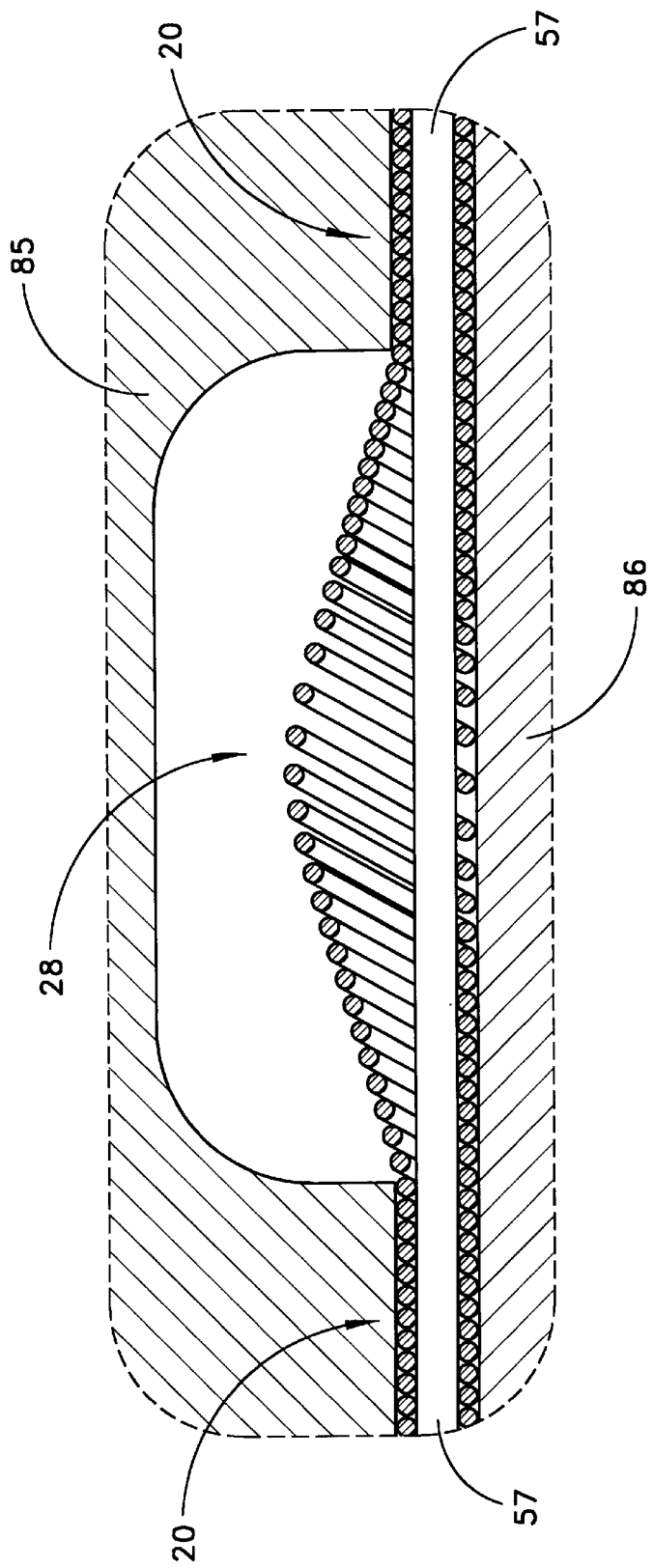
FIG. 34A is an enlarged view showing in longitudinal cross-section details of a portion of FIG. 34.
Figure 35:
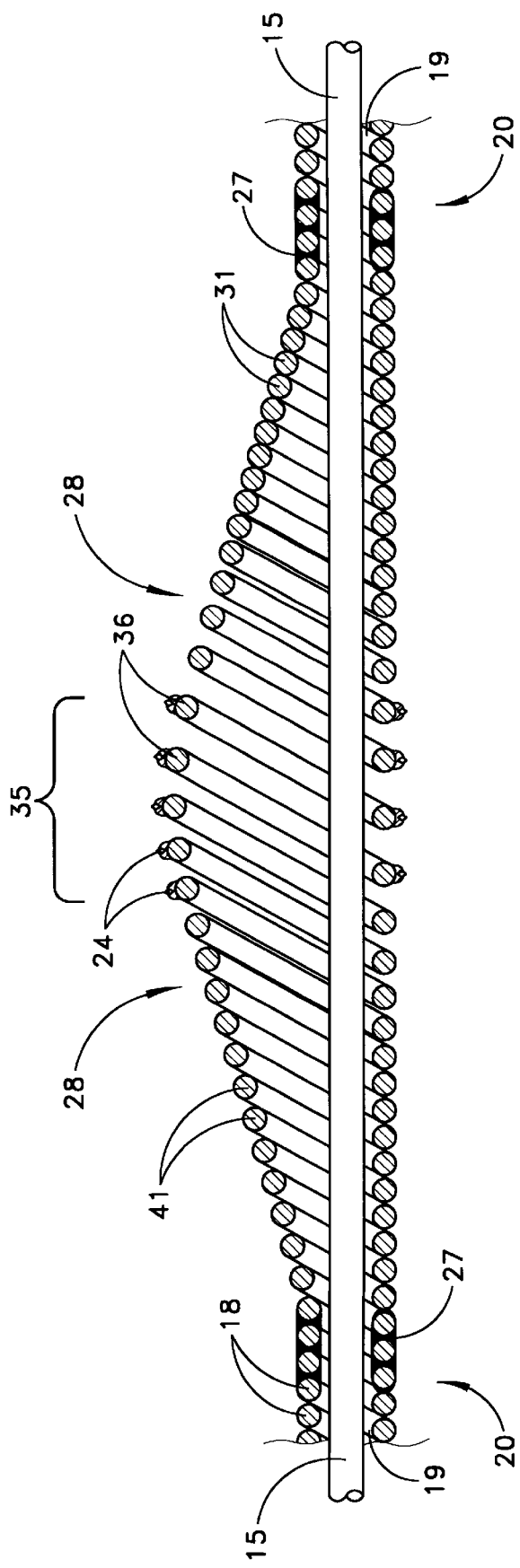
FIG. 35 is a longitudinal cross-sectional view of the enlarged diameter section of a drive shaft produced using the process illustrated in FIGS. 32–34, after abrasive has been attached to individual wire turns.

After being inelastically stretched, the enlarged diameter section 28 is placed in the second clamp 80, as is shown in FIGS. 34–34A, and finished as described above. FIG. 35 shows the resultant enlarged diameter section 28 after the remaining processing has been completed, including attachment of abrasive particles 24 and markers 27.

Figure 36:
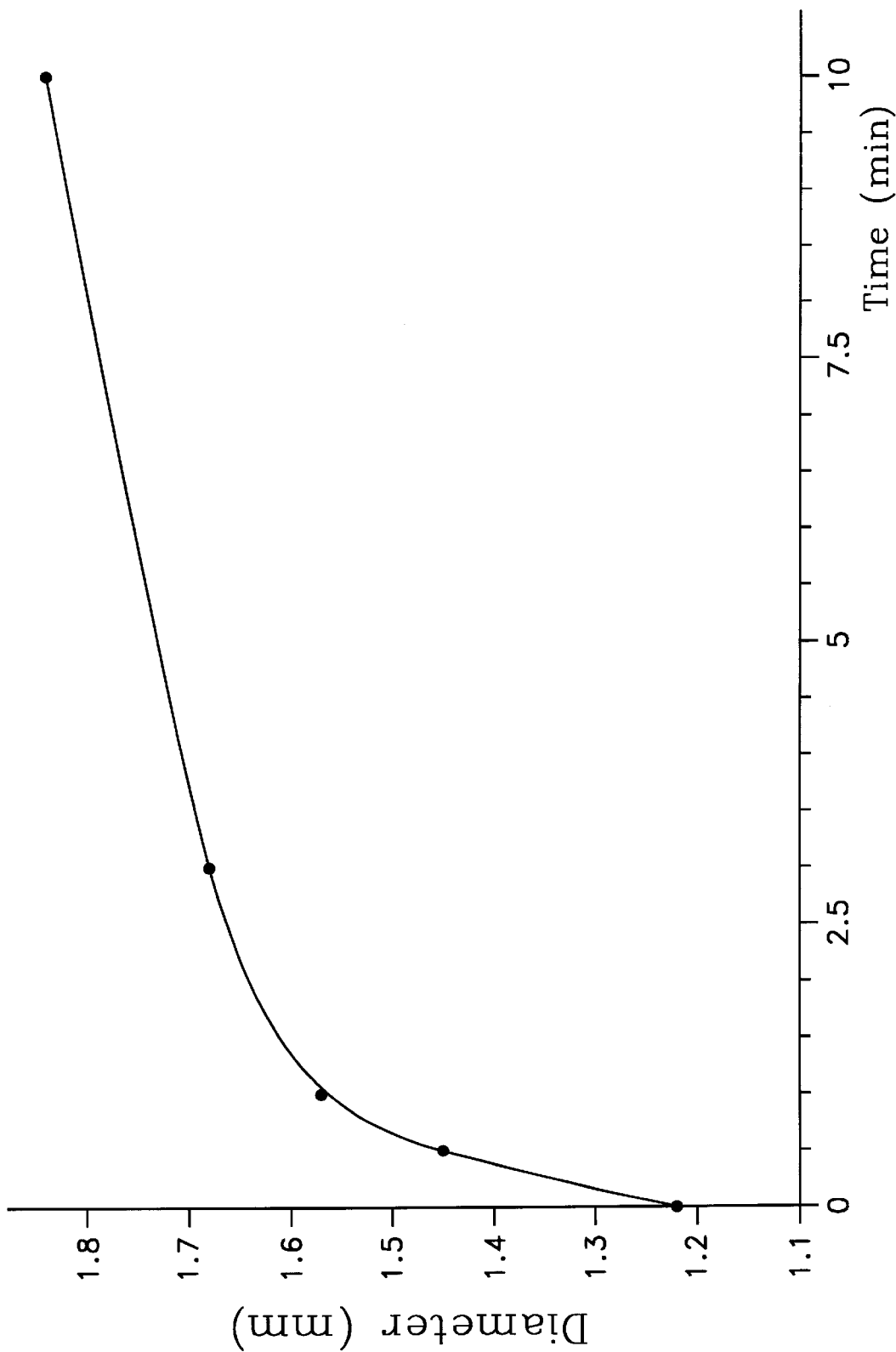
FIG. 36 is a graph of experimental data using a drive shaft having an eccentric enlarged diameter section with a diameter of 1.14 mm, showing the increase over time in the diameter of the channel opened by the rotating drive shaft.

FIG. 36 depicts experimental data of an asymmetric enlarged diameter section having a nominal diameter of 1.14 mm (including the abrasive particles) being used to open a passageway in calcite (a stone comprised predominantly of $CaCO_3$) at a rotational speed of about 140,000 rpm. The experiment was initiated on test stones having 10 mm long passageways with diameters of just over 1.2 mm. The graph indicates that the asymmetric enlarged diameter section, having a nominal diameter of 1.14 mm, was able to open the passageway to a diameter of about than 1.8 mm. The data illustrates the time dependence of the procedure—i.e., an operator can control the diameter to which the stenosis will be opened by controlling the length of time the rotating asymmetric enlarged diameter section is moved back and forth across the stenosis. The data also illustrates the ability of the device to open a stenosis to a diameter substantially larger than the nominal diameter of the eccentric enlarged diameter section.

Figure 37:
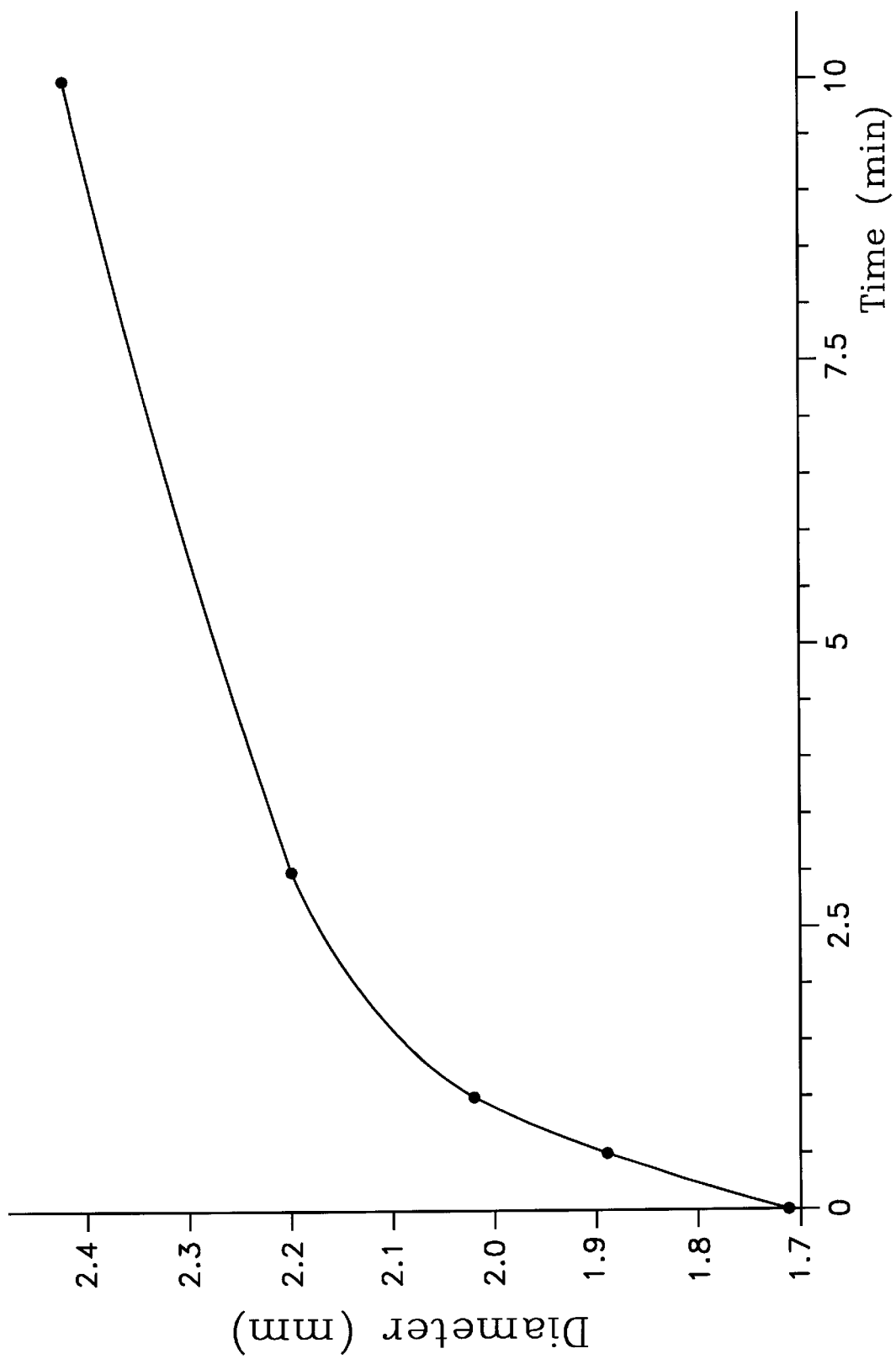
FIG. 37 is a graph of experimental data using a drive shaft having an eccentric enlarged diameter section with a diameter of 1.58 mm, showing the increase over time in the diameter of the channel opened by the rotating drive shaft.

FIG. 37 is a graph of similar experimental data using a drive shaft having an asymmetrical enlarged diameter section with a diameter of 1.58 mm, rotated at a speed of about 95,000 rpm. Within ten minutes the device was able to open the passageway to about 2.4 mm.

Figure 38:
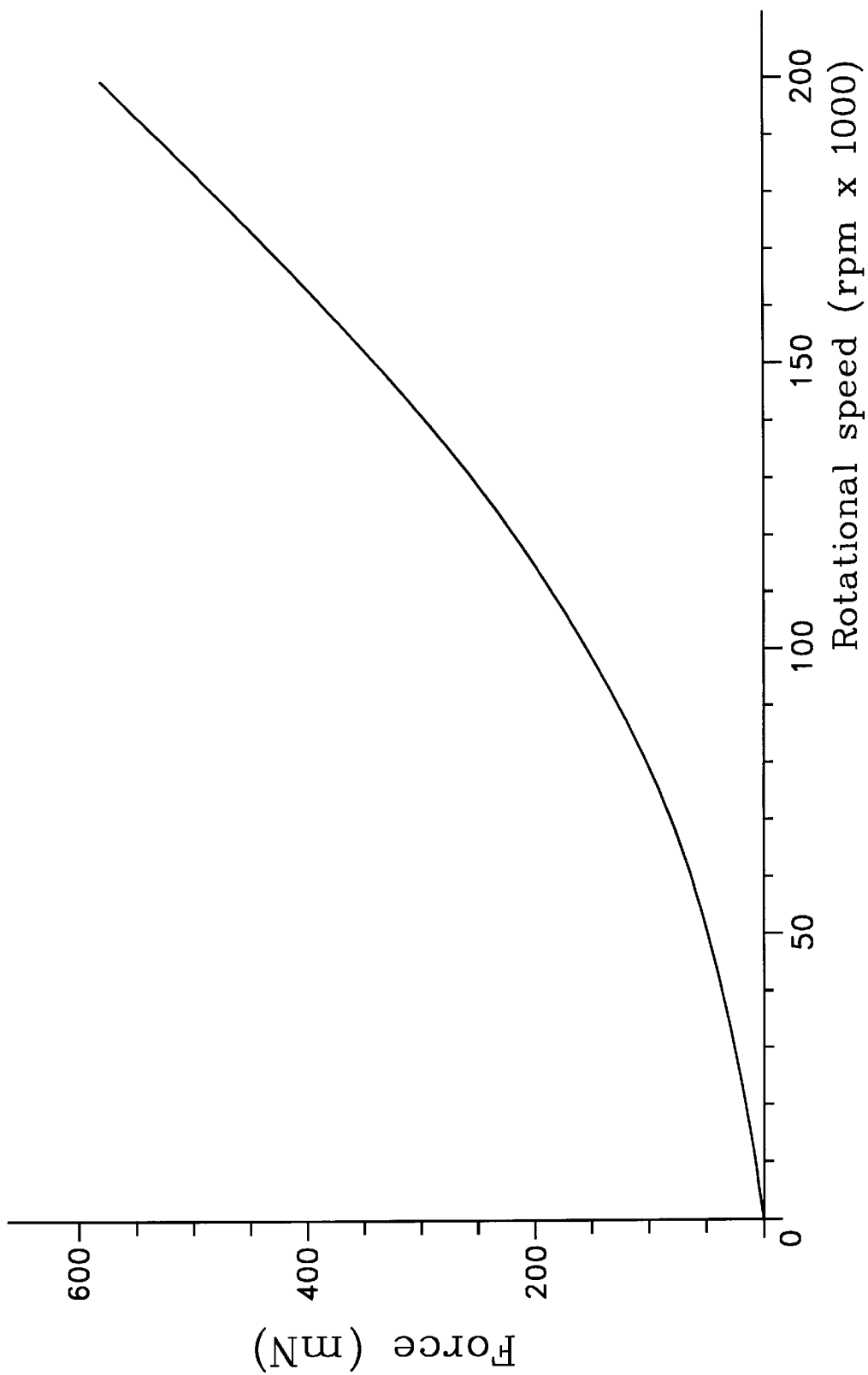
FIG. 38 is a graph illustrating the centrifugal force as a function of rotational speed of a drive shaft having an eccentric enlarged diameter section with a diameter of 1.2 mm.

The graph shown in FIG. 38 illustrates calculations of the maximum centrifugal force $F_c$ with which a tissue removing surface of an asymmetrical enlarged diameter section, having a maximum diameter of about 1.2 mm, can press against a surface of a stenosis at rotational speeds up to about 200,000 rpm. Controlling this force $F_c$ provides control over the rapidity with which tissue is removed, control over the maximum diameter to which the device will open a stenosis, and improved control over the particle size of the tissue being removed.

Figure 39:
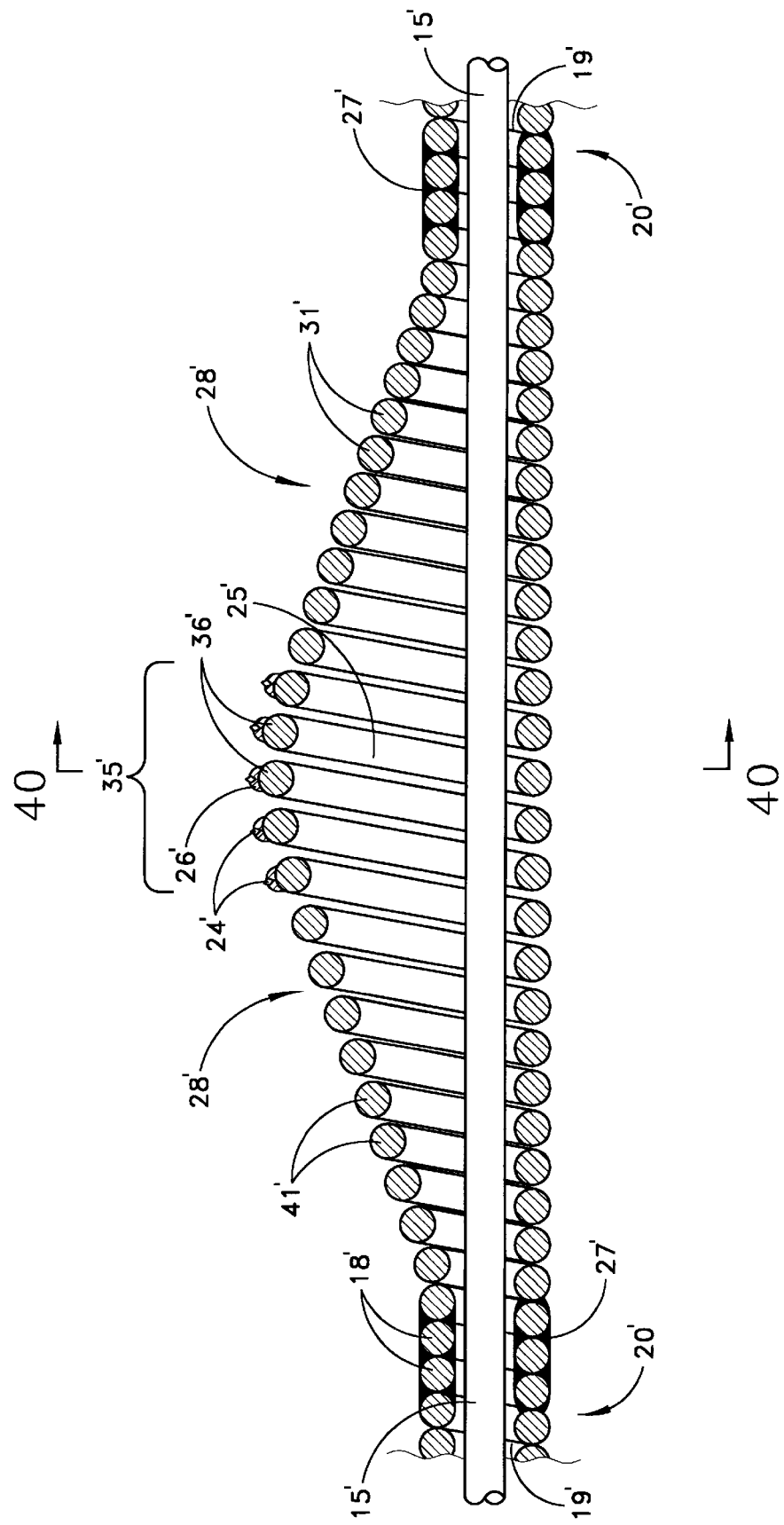
FIG. 39 is a longitudinal cross-sectional view of an alternate embodiment of the invention made from a single helically wound wire.
Figure 40:
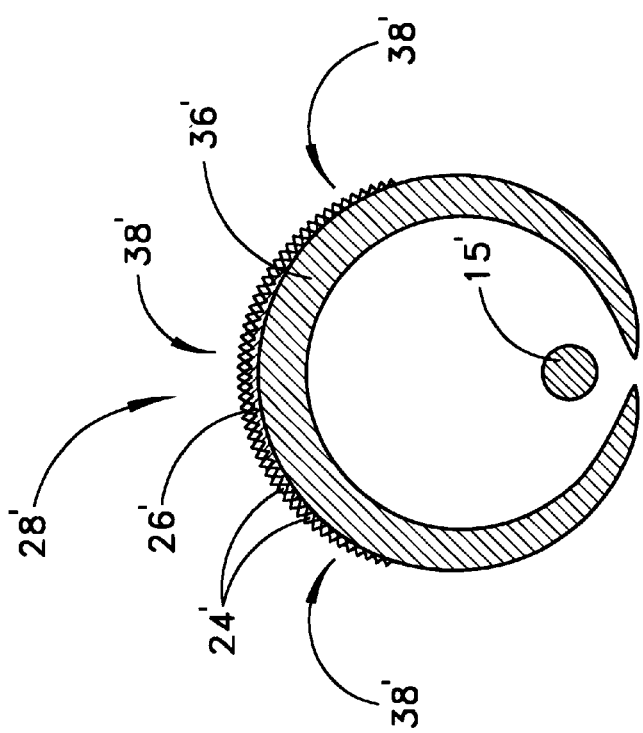
FIG. 40 is a schematic representation of a transverse cross-section of FIG. 39, taken along lines 40—40 thereof.

FIGS. 39–40 illustrate an alternate embodiment of the invention made from a single strand of helically wound wire. (In this embodiment all reference numbers correspond to elements of the above embodiments, but are marked with the prime symbol.) The drive shaft 20' of this embodiment may be made by winding the wire 18' about a suitable mandrel, as described above. Alternately, the drive shaft 20' may be made using spring coiling machine technology, such as that which is commercially available from, e.g., WMC WAFIOS Machinery Corp. of Branford, Conn. (affiliated with WAFIOS Maschinenfabrik GmbH & Co., of Reutlingen, Germany). Spring coiling machines are capable of coiling wire without the use of a mandrel—hence, a wide variety of shapes (particularly symmetrical shapes) can be coiled without the need to construct or remove a mandrel. A symmetrical enlarged diameter segment of the drive shaft formed by such spring coiling technology may be deformed to the shape shown in FIG. 39 using the clamping techniques described above, and then heat treated to give the wire turns a set in the desired asymmetrical shape.

The embodiment depicted in FIGS. 39–40 also differs from prior embodiments of the invention described above in that the abrasive segment 38' (i.e., the portion of the enlarged diameter tissue removal section 28' on which the abrasive material secured) extends only part of the way around the wire turns of the enlarged diameter tissue removal section 28' of the drive shaft 20'.

While a preferred embodiment of the present invention has been described, it should be understood that various changes, adaptations and modifications may be made therein without departing from the spirit of the invention and the scope of the appended claims.

What is claimed is:

1. A method of manufacturing a drive shaft having an asymmetrical tissue removal section comprising the steps of:

helically winding one or more strands of wire to form an elongated, flexible drive shaft having wire turns defining an enlarged diameter tissue removal section having an initial shape; and deforming at least a portion of the enlarged diameter tissue removal section to a desired shape that is asymmetrical with respect to a rotational axis of the drive shaft.

2. The method of claim 1 wherein the enlarged diameter tissue removal section is helically wound to an initial shape that is symmetrical with respect to the rotational axis of the drive shaft.

3. The method of claim 1 wherein the enlarged diameter tissue removal section is deformed so that in its desired shape an outer surface of each wire turn of the enlarged diameter tissue removal section includes a point that is collinear with a point on the outer surface of each other wire turn of the enlarged diameter tissue removal section, such points defining a straight line that is parallel to the rotational axis of the drive shaft.

4. The method of claim 1 wherein the enlarged diameter tissue removal section is deformed so that in its desired shape all wire turns of the tissue removal section may be connected by an imaginary straight line which throughout its length is parallel to the rotational axis of the drive shaft.

5. The method of claim 1 wherein the enlarged diameter tissue removal section is deformed so that in its desired shape each wire turn of the enlarged diameter tissue removal section includes a point on its outer surface that is spaced the same distance from the rotational axis of the drive shaft as a point on the outer surface of each other wire turn of the enlarged diameter tissue removal section of the drive shaft.

6. The method of claim 1 wherein the deforming step includes the step of placing the enlarged diameter tissue removal section into a clamp which is sized and shaped to give the enlarged diameter tissue removal section the desired asymmetrical shape.

7. The method of claim 6 further comprising the step of heat treating the enlarged diameter tissue removal section, after it has been placed in the clamp, to give the wire turns of the enlarged diameter tissue removal section a set in the desired asymmetrical shape.

8. The method of claim 6 wherein the deforming step includes the steps of:
(a) deforming the enlarged diameter tissue removal section to an asymmetrical shape by placing it in the clamp,
(b) elastically stretching the enlarged diameter tissue removal section within the clamp and then securing it in such stretched position by tightening the clamp, and
(c) heat treating the enlarged diameter tissue removal section to give the wire turns of the enlarged diameter tissue removal section a set in such stretched position.

9. The method of claim 6 wherein the deforming step includes the steps of:
(a) stretching the enlarged diameter tissue removal section sufficiently to inelastically deform at least a middle portion of the enlarged diameter section, thereby creating spaces (of a predetermined width) between the wire turns of the middle portion of the enlarged diameter tissue removal section,
(b) deforming the enlarged diameter tissue removal section to an asymmetrical shape by placing it in the clamp, and
(c) heat treating the enlarged diameter tissue removal section to give the wire turns of the enlarged diameter tissue removal section a set in such stretched position and asymmetrical shape.

10. The method of claim 7, 8 or 9 wherein the heat treatment is at a temperature of between about 230° C. and about 600° C. for at least about ten minutes.

11. The method of claim 7, 8 or 9 wherein the heat treatment is at a temperature of between about 360° C. and about 600° C. for at least about a half hour.

12. The method of claim 7, 8 or 9 wherein the heat treatment is at a temperature of between about 470° C. and about 530° C. for at least about half an hour.

13. The method of claim 7, 8 or 9 wherein the heat treatment is at a temperature of between about 470° C. and about 530° C. for at least about an hour.

14. The method of claim 7, 8 or 9 wherein the heat treatment is conducted in an inert gas environment.

15. The method of claim 14 wherein the inert gas is argon.

16. The method of claim 7, 8 or 9 wherein the heat treatment is conducted in a gas environment of $SF_6$.

17. The method of claim 1 further comprising the step of heat treating the drive shaft after the helically winding step and before the deforming step to give the wire turns of the drive shaft a set in the initial shape.

18. The method of claim 17 wherein the heat treatment is at a temperature of between about 230° C. and about 600° C. for at least about ten minutes.

19. The method of claim 17 wherein the heat treatment is at a temperature of between about 360° C. and about 600° C. for at least about a half hour.

20. The method of claim 17 wherein the heat treatment is at a temperature of between about 540° C. and about 580° C. for at least about half an hour.

21. The method of claim 17 wherein the heat treatment is at a temperature of between about 540° C. and about 580° C. for at least about an hour.

22. The method of claim 17 wherein the heat treatment is conducted in an inert gas environment.

23. The method of claim 22 wherein the gas is argon.

24. The method of claim 17 wherein the heat treatment is conducted in a gas environment of $SF_6$.

25. A method of manufacturing a drive shaft having an asymmetrical tissue removal section comprising the steps of:
helically winding one or more strands of wire to form an elongated, flexible drive shaft having wire turns defining an enlarged diameter tissue removal section having an initial shape;
deforming at least a portion of the enlarged diameter tissue removal section to a desired shape that is asymmetrical with respect to a rotational axis of the drive shaft; and
forming an abrasive surface on at least a portion of the enlarged diameter tissue removal section.

26. The method of claim 25 wherein the abrasive surface is formed only on a portion of the enlarged diameter tissue removal section, thereby defining an abrasive segment of the enlarged diameter section of the drive shaft.

27. The method of claim 26 wherein the abrasive segment extends only part of the way around the enlarged diameter tissue removal section of the drive shaft.

28. The method of claim 25 wherein the abrasive surface is formed after the enlarged diameter tissue removal section has been deformed to the desired shape.

29. The method of claim 25 wherein the step of forming the abrasive surface includes securing abrasive particles with a bonding material to outer surfaces of at least some of the wire turns of the enlarged diameter section.

30. The method of claim 29 wherein the bonding material is gold, platinum, iridium or alloys made therefrom.

31. The method of claim 29 further comprising the step of longitudinally stretching the enlarged diameter section to create spaces between at least some of the wire turns before securing abrasive particles to the wire turns so that the abrasive particle bonding material may be applied to the wire turns without securing the wire turns to each other.

32. The method of claim 1 further comprising the step of securing several wire turns of the drive shaft to each other just distal and just proximal to the enlarged diameter section of the drive shaft.

33. The method of claim 1 wherein the winding step includes helically winding one or more strands of wire about an elongated mandrel having an enlarged diameter section with a predetermined shape, thereby forming an elongated, flexible drive shaft which has an enlarged diameter tissue removal section, defined by wire turns of the drive shaft and having an initial shape which corresponds to the shape of the enlarged diameter section of the mandrel.

34. The method of claim 33 further comprising the step of immersing at least the enlarged diameter tissue removal section of the drive shaft into an acidic solution to dissolve at least the enlarged diameter section of the mandrel from within the drive shaft.

35. The method of claim 34 wherein the enlarged diameter tissue removal section of the drive shaft is immersed in a solution containing between about 30% and about 40% nitric acid.

36. The method of claim 35 wherein the enlarged diameter tissue removal section of the drive shaft is immersed in the nitric acid for at least about four hours at a temperature of at least about 50° C.

37. The method of claim 35 wherein the enlarged diameter tissue removal section of the drive shaft is immersed in the nitric acid for at least about eight hours at a temperature of at least about 80° C.

38. The method of claim 33 further comprising the step of immersing the entire drive shaft, including the enlarged diameter tissue removal section, in a solution of at least about 10% nitric acid for at least about four hours.

39. The method of claim 33 further comprising the step of immersing the entire drive shaft, including the enlarged diameter tissue removal section, in a solution of at least about 15% nitric acid for at least about eight hours.

40. The method of claim 34 wherein the drive shaft wire and at least the enlarged diameter section of the mandrel are made from different metals, the metal of the enlarged diameter section of the mandrel being dissolvable in nitric acid without substantially adversely affecting the wire of the drive shaft.

41. The method of claim 34 wherein the enlarged diameter section of the mandrel is made from brass, and the drive shaft wire is made from stainless steel.

42. The method of claim 34 wherein the mandrel includes a round mandrel shaft to which the enlarged diameter section is secured, the mandrel shaft being made from high carbon steel.

43. A method of manufacturing a drive shaft having an asymmetrical tissue removal section comprising the steps of:

helically winding one or more strands of wire to form an elongated, flexible drive shaft having wire turns defining an enlarged diameter tissue removal section having an initial shape;

deforming the enlarged diameter tissue removal section by placing it into a clamp that is shaped and sized to give the enlarged diameter tissue removal section a desired asymmetrical shape; and heat treating the enlarged diameter tissue removal section to give the wire turns of the enlarged diameter tissue removal section a set in a desired final asymmetrical shape.

44. A method of manufacturing a drive shaft having an asymmetrical tissue removal section comprising the steps of:

helically winding one or more strands of wire to form an elongated, flexible drive shaft having wire turns which define an enlarged diameter tissue removal section having an initial shape;

deforming the enlarged diameter tissue removal section to a desired shape that is asymmetrical with respect to a rotational axis of the drive shaft; and heat treating the deformed enlarged diameter tissue removal section so that the tissue removal section retains the desired shape.

45. A method of manufacturing a drive shaft having an asymmetrical tissue removal section comprising the steps of:

helically winding one or more strands of wire to form an elongated, flexible drive shaft having wire turns which define an enlarged diameter tissue removal section having an initial shape;

deforming the enlarged diameter tissue removal section to a desired shape in which the center of mass of the enlarged diameter tissue removal section is spaced away from a rotational axis of the drive shaft; and heat treating the deformed enlarged diameter tissue removal section so that the tissue removal section retains the desired shape.

46. A method of manufacturing a drive shaft having an asymmetrical tissue removal section comprising the steps of:

helically winding one or more strands of wire about an elongated mandrel having an enlarged diameter section with a predetermined shape, thereby forming an elongated, flexible drive shaft which has an enlarged diameter tissue removal section defined by wire turns of the drive shaft and having an initial shape which corresponds to the shape of the enlarged diameter section of the mandrel;

placing a portion of the drive shaft, including the enlarged diameter tissue removal section, into a first clamp and heat treating that portion of the drive shaft (the "first heat treatment") to give the wire turns of the enlarged diameter tissue removal section an initial set, thereby preserving the initial shape of the enlarged diameter tissue removal section of the drive shaft;

removing the drive shaft from the first clamp and immersing at least the enlarged diameter tissue removal section of the drive shaft into an acidic solution to dissolve at least the enlarged diameter section of the mandrel from within the drive shaft;

deforming the enlarged diameter section of the drive shaft to an asymmetrical shape by placing a portion of the drive shaft, including the enlarged diameter tissue removal section, into a second clamp; and heat treating the clamped portion of the drive shaft (the "second heat treatment") to give wire turns of the enlarged diameter tissue removal section a set, thereby preserving the asymmetrical shape of the enlarged diameter section.

47. The method of claim 46 wherein the enlarged diameter tissue removal section is helically wound to the initial shape that is symmetrical with respect to the rotational axis of the drive shaft.

48. The method of claim 46 wherein the enlarged diameter tissue removal section is deformed so that in its desired shape an outer surface of each wire turn of the enlarged diameter tissue removal section includes a point that is collinear with a point on the outer surface of each other wire turn of the enlarged diameter tissue removal section, such points defining a straight line that is parallel to the rotational axis of the drive shaft.

49. The method of claim 46 wherein the enlarged diameter tissue removal section is deformed so that in its desired shape all wire turns of the tissue removal section may be connected by an imaginary straight line which throughout its length is parallel to the rotational axis of the drive shaft.

50. The method of claim 46 wherein the enlarged diameter tissue removal section is deformed so that in its desired shape each wire turn of the enlarged diameter tissue removal section includes a point on its outer surface that is spaced the same distance from the rotational axis of the drive shaft as a point on the outer surface of each other wire turn of the enlarged diameter tissue removal section of the drive shaft.

51. The method of claim 46 wherein each heat treatment is at a temperature of between about 230° C. and about 600° C. for at least about ten minutes.

52. The method of claim 46 wherein each heat treatment is at a temperature of between about 360° C. and about 600° C. for at least about a half hour.

53. The method of claim 46 wherein the first heat treatment is at a temperature of between about 540° C. and about 580° C. for at least about half an hour.

54. The method of claim 46 wherein the first heat treatment is at a temperature of between about 540° C. and about 580° C. for at least about an hour.

55. The method of claim 46 wherein the second heat treatment is at a temperature of between about 470° C. and about 530° C. for at least about half an hour.

56. The method of claim 46 wherein the second heat treatment is at a temperature of between about 470° C. and about 530° C. for at least about an hour.

57. The method of claim 46 wherein each heat treatment is conducted in an inert gas environment.

58. The method of claim 57 wherein the inert gas is argon.

59. The method of claim 46 wherein each heat treatment is conducted in a gas environment of $SF_6$.

60. The method of claim 46 wherein the drive shaft wire and at least the enlarged diameter section of the mandrel are made from different metals, the metal of the enlarged diameter section of the mandrel being dissolvable in an acid without substantially adversely affecting the wire of the drive shaft.

61. The method of claim 60 wherein the metal of the enlarged diameter section of the mandrel is dissolvable in nitric acid.

62. The method of claim 46 wherein the enlarged diameter section of the mandrel is made from brass, and the drive shaft wire is made from stainless steel.

63. The method of claim 46 wherein the mandrel includes a round mandrel shaft to which the enlarged diameter section is secured, the mandrel shaft being made from high carbon steel.

64. The method of claim 46 wherein the enlarged diameter tissue removal section of the drive shaft is immersed in a solution containing between about 30% and about 40% nitric acid.

65. The method of claim 64 wherein the enlarged diameter tissue removal section of the drive shaft is immersed in the nitric acid for at least about four hours at a temperature of at least about 50° C.

66. The method of claim 64 wherein the enlarged diameter tissue removal section of the drive shaft is immersed in the nitric acid for at least about eight hours at a temperature of at least about 80° C.

67. The method of claim 46 further comprising the step of immersing the entire drive shaft, including the enlarged diameter tissue removal section, in a solution of at least about 10% nitric acid for at least about four hours.

68. The method of claim 46 further comprising the step of immersing the entire drive shaft, including the enlarged diameter tissue removal section, in a solution of at least about 15% nitric acid for at least about eight hours.

69. The method of claim 46 wherein the entire drive shaft is immersed in the acidic solution to remove the mandrel from within the drive shaft.

70. The method of claim 46 further comprising the step of heat treating the entire drive shaft at a temperature of between about 200° C. and about 400° C.

71. The method of claim 70 wherein the 200° C.–400° C. heat treatment is conducted after the second heat treatment.

72. The method of claim 46 further comprising the step of heat treating the entire drive shaft at a temperature of between about 250° C. and about 350° C.

73. The method of claim 46 further comprising the step of forming an abrasive surface on at least a portion of the enlarged diameter tissue removal section of the drive shaft.

74. The method of claim 73 wherein abrasive surface is formed only on a portion of the enlarged diameter tissue removal section, thereby defining an abrasive segment of the enlarged diameter section of the drive shaft.

75. The method of claim 74 wherein the abrasive segment extends only part of the way around the enlarged diameter tissue removal section of the drive shaft.

76. The method of claim 73 wherein the step of forming the abrasive surface includes securing abrasive particles with a bonding material to outer surfaces of at least some of the wire turns of the enlarged diameter section.

77. The method of claim 76 wherein the bonding material is gold, platinum, iridium or alloys made therefrom.

78. The method of claim 76 further comprising the step of longitudinally stretching the enlarged diameter section to create spaces between at least some of the wire turns before securing abrasive particles to the wire turns so that the abrasive particle bonding material may be applied to the wire turns without securing the wire turns to each other.

79. The method of claim 46 wherein the deforming step includes the steps of:
(a) deforming the enlarged diameter tissue removal section to an asymmetrical shape by placing it in the second clamp,
(b) elastically stretching the enlarged diameter tissue removal section within the second clamp and then securing it in such stretched position by tightening the second clamp, and
(c) heat treating the enlarged diameter tissue removal section to give the wire turns of the enlarged diameter tissue removal section a set in such stretched position.

80. The method of claim 46 wherein the deforming step includes the steps of:
(a) stretching the enlarged diameter tissue removal section sufficiently to inelastically deform at least a middle portion of the enlarged diameter section, thereby creating spaces (of a predetermined width) between the wire turns of the middle portion of the enlarged diameter tissue removal section,
(b) deforming the enlarged diameter tissue removal section to an asymmetrical shape by placing it in the second clamp, and
(b) heat treating the enlarged diameter tissue removal section to give the wire turns of the enlarged diameter tissue removal section a set in such stretched position and asymmetrical shape.

81. The method of claim 34 wherein the acidic solution is a solution including nitric acid.

* * * * *